United States Patent
Kim et al.

(10) Patent No.: US 11,649,231 B2
(45) Date of Patent: May 16, 2023

(54) COMPOUND AS MTOR INHIBITOR AND USE THEREOF

(71) Applicants: MEDICINAL BIOCONVERGENCE RESEARCH CENTER, Gyeonggi-do (KR); INDUSTRY-ACADEMIC COOPERATION FOUNDATION, YONSEI UNIVERSITY, Seoul (KR)

(72) Inventors: Sunghoon Kim, Gyeonggi-do (KR); Jong Hyun Kim, Seoul (KR); Gyoonhee Han, Seoul (KR); Jung Min Han, Seoul (KR); Chulho Lee, Seoul (KR)

(73) Assignees: MEDICINAL BIOCONVERGENCE RESEARCH CENTER, Gyeonggi-do (KR); INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 17/080,497

(22) Filed: Oct. 26, 2020

(65) Prior Publication Data

US 2021/0292314 A1    Sep. 23, 2021

Related U.S. Application Data

(63) Continuation of application No. PCT/KR2019/005108, filed on Apr. 26, 2019.

(30) Foreign Application Priority Data

Apr. 26, 2018  (KR) .................. 10-2018-0048774

(51) Int. Cl.
*C07D 417/14* (2006.01)
*C07D 417/06* (2006.01)

(52) U.S. Cl.
CPC .......... *C07D 417/14* (2013.01); *C07D 417/06* (2013.01)

(58) Field of Classification Search
CPC .................................................. C07D 417/06
See application file for complete search history.

(56) References Cited

U.S. PATENT DOCUMENTS

| | | | | |
|---|---|---|---|---|
| 3,615,608 | A * | 10/1971 | Van Lare | G03C 1/4853 430/543 |
| 8,901,307 | B2 * | 12/2014 | Dakin | C07D 417/12 546/209 |
| 10,677,806 | B2 | 6/2020 | Kim et al. | |
| 11,378,572 | B2 | 7/2022 | Kim et al. | |
| 11,442,057 | B2 | 9/2022 | Kim et al. | |
| 2004/0214872 | A1 * | 10/2004 | Suto | A61K 31/425 514/369 |
| 2005/0065066 | A1 * | 3/2005 | Kaarsholm | C07K 14/62 514/6.3 |
| 2019/0033295 | A1 | 1/2019 | Kim et al. | |
| 2019/0277865 | A1 | 9/2019 | Kim et al. | |
| 2020/0141923 | A1 | 5/2020 | Kim et al. | |

FOREIGN PATENT DOCUMENTS

| | | | |
|---|---|---|---|
| CN | 102078318 A | 6/2011 | |
| JP | 2003264010 | * 9/2003 | |
| WO | WO-2004093803 A2 | * 11/2004 | ............ A61K 31/41 |
| WO | WO 2011/063602 A1 | 6/2011 | |
| WO | WO 2015-027307 A1 | 3/2015 | |
| WO | WO 2017-176040 A1 | 10/2017 | |

OTHER PUBLICATIONS

Goldfarb CA 151:115085. (Year: 2009).*
Goldfarb 1, CA 151:115084. (Year: 2009).*
Goldfarb II, CA 151:115083. (Year: 2009).*
International Search Report corresponding to International application No. PCT/KR2019/005108 dated Aug. 6, 2019.
Insuasty et al., "Synthesis, Antifungal and Antitumor Activity of Novel (Z)-5-Hetarylmethylidene-1.3-thiazol-4-ones and (Z)-5-Ethylidene-1.3-thiazol-4-ones," Molecules, vol. 18, pp. 5482-5497 (2013).
English Translation of the Written Opinion of the International Searching Authority Corresponding to International Application No. PCT/KR 2019/005108 dated Aug. 6, 2019.
International Preliminary Report on Patentability Corresponding to International Application No. PCT/KR 2019/005108 dated Oct. 27, 2020.
Zoncu et al., "mTOR: from growth signal integration to cancer, diabetes and ageing." Nature Rev. Mol. Cell Biol., vol. 12, pp. 21-35 (2011).
Ravikumar et al., "Inhibition of mTOR induces autophagy and reduces toxicity of polyglutamine expansions in fly and mouse models of Huntington disease." Nat. Genet., vol. 36(6), pp. 585-595 (2004).
Pan et al., "Neuroprotection of rapamycin in lactacystin-induced neurodegeneration via autophagy enhancement." Neurobiol. Dis., vol. 32(1), pp. 16-25 (2008).
Sadowski et al., "Role of mTOR inhibitors in epilepsy treatment." Pharmacological Reports, vol. 67(3), pp. 636-646 (2015).
Shaw et al., "mTOR signaling: RAG GTPases transmit the amino acid signal." Trends in Biochemical Sciences, vol. 33, pp. 565-568 (2008).
Hill et al., "Neurobiology of chronic mild stress: Parallels to major depression." Neurosci. Biobehav. Rev., vol. 36, pp. 2085-2117 (2012).

(Continued)

*Primary Examiner* — Zinna Northington Davis
(74) *Attorney, Agent, or Firm* — Jenkins, Wilson, Taylor & Hunt, P.A.

(57) ABSTRACT

The present invention relates to a novel compound as an mTOR inhibitor and a use thereof and, more specifically, to a novel compound represented by formula 1 that exhibits mTOR inhibitory activity and a pharmaceutical composition comprising same as an active ingredient for preventing or treating brain diseases associated with an mTOR pathway.

8 Claims, 8 Drawing Sheets
(1 of 8 Drawing Sheet(s) Filed in Color)

(56) References Cited

OTHER PUBLICATIONS

Zhu et al., "Glycine site N-methyl-d-aspartate receptor antagonist 7-CTKA produces rapid antidepressant-like effects in male rats." J. Psychiatry Neurosci., vol. 38, pp. 306-316 (2013).
Chandran et al., "Reduced phosphorylation of the mTOR signaling pathway components in the amygdala of rats exposed to chronic stress." Prog. Neuropsychopharmacol. Biol. Psychiatry, vol. 40, pp. 240-245 (2013).
Bove et al., "Fighting neurodegeneration with rapamycin: mechanistic insights." Nature Reviews Neuroscience, vol. 12, pp. 437-452 (2011).
Gilbert et al., "5-((1H-pyrazol-4-yl)methylene)-2-thioxothiazolidin-4-one inhibitors of ADAMTS-5", Biorganic & Medicinal Chemical Letters, vol. 17, pp. 1189-1192 (2007).
Hüttel, et al. "Synthese einiger Athylamine und Alanine der Pyrazol- und 1,2,3-Triazol-Reihe", Justus Lieblen der Chemie, vol. 585, pp. 115-125 (1953).
Extended European Search Report corresponding European Application No. 1979200.7 dated Nov. 26, 2021.
Lipton et al. "The Neurology of mTOR", Neuron Review, vol. 84, pp. 275-291, Oct. 22, 2014.
Office Action corresponding to Korean Patent application No. 10-2019-0049372 dated Oct. 27, 2020.
Aghaie et al., "Rapamycin attenuates depressiona and anxiety-like behaviors through modulation of the NLRP3 pathway in pentylenetetrazole-kindled male Wistar rats", Fundam Clin Pharmacol, vol. 35, pp. 1045-1054 (2021).
Ehninger and Silva, "Rapamycin for treating Tuberous sclerosis and Autism spectrum disorders", Trends in Molecular Medicine, vol. 17, pp. 78-87 (2011).
Iacobas et al., "Oral Rapamycin in the Treatment of Patients with Hamartoma Syndromes and PTEN Mutation", Pediatr Blood Cancer, vol. 57, pp. 321-323 (2011).
Kim, "Mammalian target of rapamycin inhibitors for treatment in tuberous sclerosis", Korean J Pediatr, vol. 54, pp. 241-245 (2011).
Kotajima-Murakami et al., "Effects of rapamycin on social interaction deficits and gene expression in mice exposed to valproic acid in utero", Molecular Brain, vol. 12, pp. 1-14 (2019).
Santini et al., "Inhibition of mTOR Signaling in Parkinson's Disease Prevents L-DOPA-Induced Dyskinesia", www.sciencesignaling.org, vol. 2, ra36 (2009).
Squarize et al., "Chemoprevention and Treatment of Experimental Cowden's Disease by mTOR Inhibition with Rapamycin", Cancer Res, vol. 68, pp. 7066-7072 (2008).
Weiss et al., "Sirolimus for progressive neurofibromatosis type 1-associated plexiform neurofibromas: a Neurofibromatosis Clinical Trials Consortium phase II study", Neuro-Oncology, vol. 17, pp. 596-603 (2015).
Zak et al., "Infantile Lhermitte-Duclos Disease Treated Successfully with Rapamycin", Journal of Child Neurology, vol. 32, pp. 322-326 (2017).
Zhou et al., "mTOR Inhibition Ameliorates Cognitive and Affective Deficits Caused by Disc1 Knockdown in Adult-Born Dentate Granule Neurons", Neuron, vol. 77, pp. 647-654 (2013).

* cited by examiner

COMPOUND AS MTOR INHIBITOR AND USE THEREOF

This application is a continuation of PCT International Application No. PCT/KR2019/005108, filed Apr. 26, 2019, incorporated herein by reference in its entirety, which claims priority to Korean Patent Application No. 10-2018-0048774, filed on Apr. 26, 2018, incorporated herein by reference in its entirety.

The present application claims priority from and the benefit of Korean Patent Application No. 10-2018-0048774 filed on Apr. 26, 2018, which is hereby incorporated by reference for all purposes as if fully set forth herein.

The present invention relates to novel compounds as mTOR inhibitor and uses thereof, more specifically, it relates to novel compounds represented by Formula 1 showing mTORC1 inhibitory activity and a pharmaceutical composition for preventing or treating brain diseases related to mTOR pathway comprising the same as an active ingredient.

BACKGROUND ART

Amino acids are not only used as raw materials for protein synthesis, but also as nutrients that regulate protein metabolism. The action of amino acids available in the cell is mediated by mTORC1 (mechanistic target of rapamycin complex 1), and mTORC1 not only regulates various intracellular responses such as protein synthesis, autodigestion, and cell growth, but also closely related to various human diseases such as cancer, obesity, diabetes and neurodegenerative diseases.

mTOR (a mammalian target of rapamycin), also known as FRAP (FKBP12 and rapamycin-related protein), is a 289-kDa serine/threonine kinase of the PIKK (phosphoinositide 3-kinase-like kinase) family, although it does not phosphorylate phospholipids.

This protein includes several domains including a C-terminal kinase domain, FKBP12-rapamycin binding domain, a 20 N-terminal HEAT repeat involved in protein-protein interactions, a FRAP-ATM-TRRAP (FAT) domain, and a C-terminal FAT domain that is also present in other PIKKs.

mTOR kinase is a central regulator of cell growth and proliferation, and plays an important role in cell metabolism and angiogenesis. mTOR is activated by the PI3K/Akt axis and in turn phosphorylates a downstream effector of the PI3K/Akt signaling pathway, in particular the ribosomal protein S6 kinase (S6K1) and the eukaryotic initiation factor 4E binding protein (4E-BP1), two major regulators of the cellular protein translation machinery (mTOR signaling pathway is described in Zoncu et al. (2011) Nature Rev. Mol. Cell Biol. 12, 21-35).

Meanwhile, mTORC1 regulates several upstream signals such as cell growth, protein synthesis, and regulation of growth factors. Tuberous Sclerosis Complex (TSC), which transmits growth factors and energy signals to mTORC1, is a GTPase-activating protein (GAP) for Ras-like small GTPase and Rheb, and it negatively regulates mTORC1 by facilitating GTP hydrolysis of Rheb.

Rheb can migrate to late endosomes/lysosomes and is required for amino acid-induced mTORC1 activation. In the lysosome membrane, Rag GTPases and Regulator complexes (MAPKSP1, ROBLD3 and c11orf59) act as amino acid-inducible docking sites for mTORC1.

Mammals express four types of Rag GTPases (RagA, RagB, RagC, RagD). Rag GTPases essentially mediate amino acid-induced mTORC1 activation by forming a heterodimer of RagA/C or RagB/D. The amino acid induces mTORC1 to move to the lysosome, and in the lysosome, the Rag heterodimer containing GTP-bound RagB interacts with mTORC1.

Leucine and glutamine can activate mTORC1 by Rag GTPase-dependent and independent mechanisms, respectively. In RagA/B-deficient cells, glutamine can still activate mTORC1 via the ADP ribosylation factor 1 (ARF1) GTPase. Therefore, mTORC1 can be regulated differently by glutamine and leucine. However, the functional importance of Rag GTPase-dependent leucine signaling is not well known.

However, as the mTOR is excessively activated, tuberous sclerosis, characterized by seizures, autism, mild cognitive impairment, cortical tuber, and tumor development, occurs. About 90% of patients with tuberous sclerosis develop epilepsy, which is thought to be mainly caused by cortical tuber, but the exact mechanism is not yet known.

Epilepsy, which can be caused by tuberous sclerosis caused by excessive activation of mTOR, is one of the chronic neurological disorders. Epilepsy is a disease in which seizures and convulsions occur because electricity is generated in the brain due to irregular excitation of cranial nerve cells. Epilepsy is caused by various causes, and epidemiological studies have reported that more than one third of patients have a history of pathological changes or brain damage in the brain. And the main cause includes encephalitis, brain tumors, degenerative encephalopathy, inheritance, premature infants, and injuries before and after delivery.

The average prevalence of epilepsy is 0.5 to 1%, and it is one of the most prevalent diseases among chronic neurological diseases. According to a survey by the World Health Organization (WHO), there are about 50 million people with epilepsy worldwide, which is about 1% of the global disease burden. The prevalence of epilepsy varies according to age, and it is characterized by a high prevalence in children and the elderly. Recently, the number of epileptic patients in the elderly is increasing due to the increase in the elderly population due to the prolongation of lifespan, and the overall number of epileptic patients is expected to increase. There is no fundamental treatment method for epilepsy so far, and administration of antiepileptic drugs is the main treatment. About 70% of patients with chronic epilepsy can be controlled with antiepileptic drugs, but about 30% progress to drug-resistant epilepsy, where epileptic seizures are not controlled even with antiepileptic drug polytherapy. In order to solve this problem, new kinds of antiepileptic drugs have been continuously developed and marketed over the past 20 years, but the proportion of patients with drug-resistant epilepsy is still not decreasing. In the future, the increase in the elderly population is expected to significantly increase the social burden of epilepsy patients.

Meanwhile, in addition to epilepsy, it has been reported that Alzheimer's, Parkinson's and Huntington's disease are also related to the mTOR pathway.

The accumulation of Abeta and tau is considered to directly cause or contribute to progressive cognitive deficits in Alzheimer's disease. mTOR has been shown to play a role in these Abeta and tau-induced neurodegeneration. The mTOR pathway plays a central role in regulating protein homeostasis and thus in regulating neuronal function. Indeed, m TOR signaling regulates different forms of learning and memory. Rapamycin heals cognitive deficits and alleviates Abeta and tau pathologies by increasing autodigestion. Similarly, some mTOR signaling components may be potential biomarkers of cognitive impairment in the clinical diagnosis of Alzheimer's disease. Thus, through the regulation of autodigestion-lysosomal protein degradation, the mTOR-associated agent is highly likely to be developed as an important therapeutic agent for Alzheimer's disease.

Huntington's disease is one of nine hereditary neurodegenerative disorders caused by polyglutamine expansion. The expanded polyglutamine protein accumulates abnormally in intracellular aggregates. It has been found that mTOR is isolated from polyglutamine aggregates in cell models, transgenic mice and human brains. Isolation of mTOR impairs its kinase activity, induces autodigestion, and is a key clearance pathway for mutant huntingtin fragments. Mutant proteins in Huntington's disease aggregate in nerve cells and can cause nerve cell damage and toxicity. Rapamycin, an mTOR inhibitor, has been reported to attenuate the accumulation of huntingtin and apoptosis and protect against neurodegeneration in an animal model of Huntington's disease (Ravikumar et al., 2004. Nat Genet. 36(6):585-95). In addition, rapamycin induces an autophagy reaction, which is suggested to play a role in the scavenging of huntingtin aggregates.

Parkinson's disease (PD) is a neurodegenerative disease associated with the accumulation and aggregation of misfolded proteins. Prevention of aggregation or degradation of misfolded proteins can provide therapeutic benefits by slowing down or preventing the progression of PD. The ubiquitin proteasome system (UPS) is an important degradation mechanism that acts on aggregated proteins. It has been reported that rapamycin provides neuroprotection against dopaminergic neuronal cell death induced by the proteasome inhibitor lactacystin. It has been suggested that the rapamycin effect is mediated in part by the enhancement of autophagy through enhanced degradation of misfolded proteins (Pan et al., 2008. Neurobiol. Dis. 32(1):16-25). Thus, mTOR inhibitor compounds that can enhance autophagy may be a promising strategy for treating Parkinson's disease patients.

Meanwhile, aminoacyl-tRNA-synthetase (ARSs) are not only required for protein synthesis, but are also involved in various cellular physiological responses. ARS promotes the binding of amino acids to the corresponding tRNA. In order to maintain protein homeostasis, ARS must sensitize amino acid availability. Leucine-tRNA-synthetase (LRS) functions as a leucine sensor for mTORC1 activation by interacting with RagD GTPase and acting as a GAP for RagD GTPase.

Therefore, if a substance that inhibits the function of LRS as a leucine sensor is detected, this substance will inhibit the binding of LRS and RagD, thereby inhibiting the activation of mTORC1, resulting in an effect on potential therapeutic indications for mTOR inhibitors.

DETAILED DESCRIPTION OF THE INVENTION

Technical Problem

Accordingly, the present inventors made diligent efforts to discover novel compounds that can exhibit a therapeutic effect on mTOR pathway-related brain diseases by inhibiting mTOR activity. As a result, the present inventor discovered that compounds represented by Formula 1 herein inhibit mTOR activity and have great blood-brain barrier (BBB) permeability resulting in therapeutic effects on brain diseases related to the mTOR pathway.

Therefore, an aspect of the present invention is to provide a compound defined by Chemical Formula 1 or pharmaceutically acceptable salt thereof:

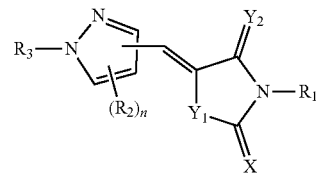

<Chemical Formula 1> wherein R1 is hydrogen; substituted or unsubstituted C1-C5 straight or branched alkyl; C2-C5 alkenyl; C3-C10 heteroarylalkyl; or C1-C5 hydroxyalkyl;

R2 is hydrogen; or substituted or unsubstituted C1-C5 straight or branched alkyl;

R3 is hydrogen; substituted or unsubstituted C1-C5 straight or branched alkyl; C6-C15 aryl; or C3-C15 heteroaryl;

X is oxygen, sulfur, or nitrogen;

Y1 and Y2 are each independently oxygen or sulfur; and n is 0, 1, or 2.

Still, another aspect of the present invention is to provide a method for preparing the compound or pharmaceutically acceptable salt thereof using Reaction Formula 1:

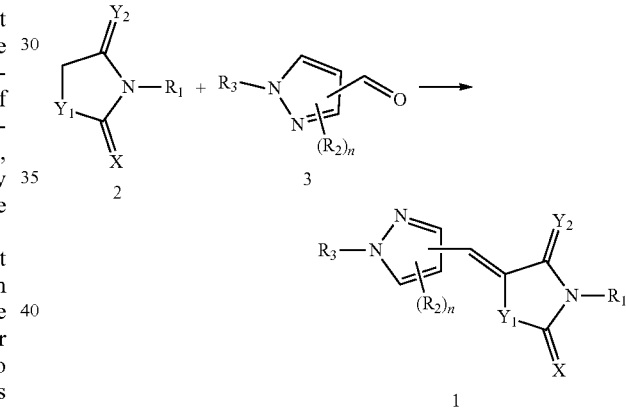

<Reaction Formula 1> wherein $R_1$, $R_2$, $R_3$, X, $Y_1$, $Y_2$ and n are described above.

Still, another aspect of the present invention is to provide a pharmaceutical composition for preventing or treating a brain disease associated with mTOR (mechanistic target of rapamycin) pathway comprising the compound or pharmaceutically acceptable salt thereof as an active ingredient.

Still, another aspect of the present invention is to provide a pharmaceutical composition for preventing or treating a brain disease associated with mTOR (mechanistic target of rapamycin) pathway consisting of the compound or pharmaceutically acceptable salt thereof as an active ingredient.

Still, another aspect of the present invention is to provide a pharmaceutical composition for preventing or treating a brain disease associated with mTOR (mechanistic target of rapamycin) pathway essentially consisting of the compound or pharmaceutically acceptable salt thereof as an active ingredient.

Still, another aspect of the present invention is to provide use of the compound or pharmaceutically acceptable salt thereof for the preparation of an agent for preventing or treating a brain disease associated with mTOR (mechanistic target of rapamycin) pathway.

Still, another aspect of the present invention is to provide a method for treating a brain disease associated with mTOR (mechanistic target of rapamycin) pathway in a subject in need thereof, the method comprising administering an effective amount of a composition comprising the compound or pharmaceutically acceptable salt thereof as an active ingredient to the subject in need thereof.

Technical Solution

Accordingly, in accordance with an aspect of the present invention, there is provided a compound defined by Chemical Formula 1 or pharmaceutically acceptable salt thereof:

<Chemical Formula 1>

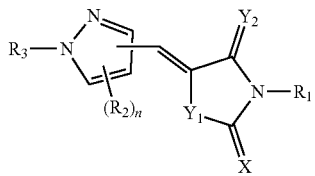

wherein R1 is hydrogen; substituted or unsubstituted C1-C5 straight or branched alkyl; C2-C5 alkenyl; C3-C10 heteroarylalkyl; or C1-C5 hydroxyalkyl;

R2 is hydrogen; or substituted or unsubstituted C1-C5 straight or branched alkyl;

R3 is hydrogen; substituted or unsubstituted C1-C5 straight or branched alkyl; C6-C15 aryl; or C3-C15 heteroaryl;

X is oxygen, sulfur, or nitrogen;

Y1 and Y2 are each independently oxygen or sulfur; and n is 0, 1, or 2.

In accordance with another aspect of the present invention, there is provided a method for preparing the compound or pharmaceutically acceptable salt thereof using Reaction Formula 1:

<Reaction Formula 1>

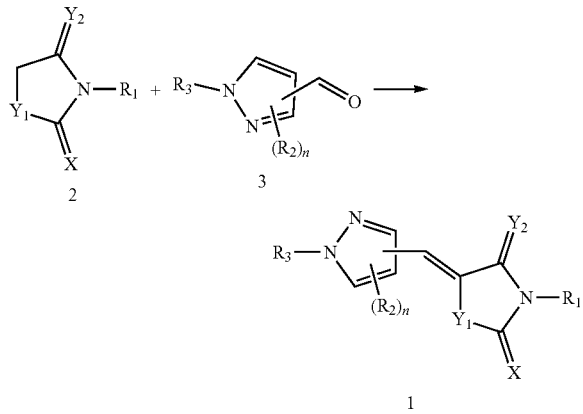

wherein $R_1$, $R_2$, $R_3$, X, $Y_1$, $Y_2$ and n are described above.

In accordance with another aspect of the present invention, there is provided a pharmaceutical composition for preventing or treating a brain disease associated with mTOR (mechanistic target of rapamycin) pathway comprising the compound or pharmaceutically acceptable salt thereof as an active ingredient.

In accordance with another aspect of the present invention, there is provided a pharmaceutical composition for preventing or treating a brain disease associated with mTOR (mechanistic target of rapamycin) pathway consisting of the compound or pharmaceutically acceptable salt thereof as an active ingredient.

In accordance with another aspect of the present invention, there is provided a pharmaceutical composition for preventing or treating a brain disease associated with mTOR (mechanistic target of rapamycin) pathway essentially consisting of the compound or pharmaceutically acceptable salt thereof as an active ingredient.

In accordance with another aspect of the present invention, there is provided use of the compound or pharmaceutically acceptable salt thereof for the preparation of an agent for preventing or treating a brain disease associated with mTOR (mechanistic target of rapamycin) pathway.

In accordance with another aspect of the present invention, there is provided a method for treating a brain disease associated with mTOR (mechanistic target of rapamycin) pathway in a subject in need thereof, the method comprising administering an effective amount of a composition comprising the compound or pharmaceutically acceptable salt thereof as an active ingredient to the subject in need thereof.

Hereinafter, the present invention will be described in detail.

In the present invention, the "alkyl" refers to an aliphatic hydrocarbon group that may be linear or branched, including 1 to 5 carbon atoms in the chain. Preferred alkyl groups contain 1 to 3 carbon atoms in the chain. More preferred alkyl groups contain about 1, 2 or 3 carbon atoms in the chain. Branched means that one or more lower alkyl groups, such as methyl, ethyl or propyl, are attached to a linear alkyl chain. "Low alkyl" means a group having 1 to 5 carbon atoms in the chain, which may be straight or branched. "Alkyl" may be unsubstituted or may be optionally substituted by one or more substituents, which may be the same or different.

In the present invention, the "alkenyl" refers to a monovalent linear or branched hydrocarbon radical having 2 to 5 carbon atoms and one or more double bonds in the chain, examples of which include ethenyl, propenyl, 1-but-3-enyl, 1-pent-3-enyl, 1-hex-5-enyl, and the like, but are not limited thereto, wherein the alkenyl radical may be independently optionally substituted by one or more of the substituents described in the present invention, including radicals having "cis" and "trans" orientations, or alternatively "E" and "Z" orientations do. "Alkenyl" may be unsubstituted or may be optionally substituted by one or more substituents, which may be the same or different.

In the present invention, the "aryl" is a single ring (eg, phenyl), multiple rings (eg, biphenyl) or multiple condensed rings (at least one of which is aromatic; eg, 1,2,3,4-tetrahydronaphthyl, naphthyl) represents a monovalent aromatic carbocyclic radical, which may be mono-, di- or tri-substituted with any substituent.

In the present invention, the "heteroaryl" refers to a monovalent aromatic radical having a 5-, 6- or 7-membered ring containing 1 to 4 heteroatoms selected from nitrogen, oxygen, or sulfur, and including a fused ring system having 5 to 15 atoms (at least one of which is aromatic). Examples of the heteroaryl group include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, Quinolinyl, isoquinolinyl, indolyl, benzimidazolyl, benzofuranyl, cinnolinyl, indazolyl, indozinyl, phthalazinyl, pyridazinyl, triazinyl, isoindolyl, pteridinyl, furinyl, oxadiazolyl, triazolyl, thiadiazolyl, thiadiazolyl, furazanyl, benzofurazolyl, benzothiophenyl, benzothiazolyl, benzoxazolyl, quinazolinyl, quinoxalinyl, naphthyridinyl and furopyridinyl. Spiro moieties are also included within the scope of the above definition. The heteroaryl group may be mono-, di- or tri-substituted with any substituent.

In the present invention, the "heteroarylalkyl" refers to an alkyl moiety (as defined above) substituted with a heteroaryl moiety (as defined above). More preferred heteroarylalkyl radicals may be 5-membered or 6-membered heteroaryl-$C_{1-3}$-alkyl. Heteroarylalkyl may be mono-, di- or tri-substituted with any substituent.

In the present invention, the "hydroxyalkyl" refers to a linear or branched monovalent hydrocarbon radical substituted with one or two hydroxy groups and containing 1 to 5 carbon atoms, for example, but not limited thereto, hydroxy methyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl, 2-(hydroxymethyl)-3-hydroxypropyl and the like.

In the present invention, the "halogen" means a fluorine atom, a chlorine atom, a bromine atom or an iodine atom.

When the groups disclosed in the present invention are expressed as "substitution", these groups may be substituted with any suitable substituents or substituents. Illustrative examples of substituents include those that can be found in the example compound and embodiment example disclosed in the present invention, and halogen (chloro, iodo, bromo or fluoro group), alkyl, hydroxyl, alkoxy, alkoxyalkyl, amino, alkyl Amino, carboxy, nitro, ano, thiol, thioether, imine, imide, amidine, guanidine, enamine, aminocarbonyl, acylamino, phosphonato, phosphine, thiocarbonyl, sulfonyl, sulfone, sulfonamide, ketone, aldehyde, ester, urea, urethane, oxime, hydroxylamine, alkoxyamine, aralkoxyamine, N-oxide, hydrazine, hydrazide, hydrazone, azide, isocyanate, isothiocyanate, cyanate, thiocyanate, etc. are mentioned.

In the formula 1 of the present invention, the $R_1$ is preferably hydrogen; Substituted or unsubstituted $C_1$~$C_3$ linear or branched alkyl; $C_2$~$C_3$ alkenyl; $C_3$~$C_6$ heteroarylalkyl; Or it may be a $C_1$~$C_3$ straight or branched hydroxyalkyl, more preferably hydrogen; Substituted or unsubstituted $C_1$~$C_2$ linear alkyl; $C_2$~$C_3$ alkenyl; $C_3$~$C_5$ heteroarylalkyl; Or it may be a $C_1$~$C_2$ linear hydroxyalkyl, most preferably hydrogen, methyl, ethyl, ethenyl, propenyl, furyl methyl and may be selected from the group consisting of hydroxyethyl.

In the formula 1 of the present invention, the R2 is preferably hydrogen; Or it may be a substituted or unsubstituted $C_1$~$C_3$ linear or branched alkyl, more preferably a substituted or unsubstituted $C_1$~$C_2$ alkyl, most preferably selected from the group consisting of hydrogen, methyl and ethyl.

In the formula 1 of the present invention, the $R_3$ is preferably substituted or unsubstituted $C_1$~$C_3$ linear or branched alkyl; $C_6$~$C_{10}$ aryl; Or it may be a $C_3$~$C_{10}$ heteroaryl, more preferably a substituted or unsubstituted $C_1$~$C_2$ alkyl; $C_6$~$C_{10}$ aryl; Or it may be a $C_3$~$C_5$ heteroaryl, and most preferably may be selected from the group consisting of substituted or unsubstituted methyl, phenyl, naphthyl and pyridyl.

When the R3 is substituted in the formula 1 of the present invention, the substituent is preferably halogen; $C_1$~$C_5$ straight or branched alkyl; And it may be selected from the group consisting of $C_1$~$C_5$ alkoxy, more preferably halogen; $C_1$~$C_4$ straight or branched alkyl; And it may be selected from the group consisting of $C_1$~$C_3$ alkoxy, most preferably chlorine, fluorine, methyl, butyl, isopropyl and may be selected from the group consisting of methoxy.

In the formula 1 of the present invention, preferably, $Y_1$ may be sulfur and $Y_2$ may be oxygen.

In the present invention, the compound of Formula 1 may be selected from the following compounds.

(5Z)-5-[(1-phenylpyrazol-4-yl)methylene]-2-thioxo-thiazolidin-4-one, (5Z)-3-(2-furylmethyl)-5-[(1-methylpyrazol-4-yl)methylene]-2-thioxo-thiazolidin-4-one, (5Z)-3-methyl-5-[(1-phenylpyrazol-4-yl)methylene]-2-thioxo-thiazolidin-4-one, (5Z)-3-ethyl-5-[(1-phenylpyrazol-4-yl)methylene]-2-thioxo-thiazolidin-4-one, (5Z)-3-allyl-5-[(1-phenylpyrazol-4-yl)methylene]-2-thioxo-thiazolidin-4-one, (5Z)-5-[[1-(2-fluorophenyl)pyrazol-4-yl]methylene]-2-thioxo-thiazolidin-4-one, (5Z)-5-[[1-(3-fluorophenyl)pyrazol-4-yl]methylene]-2-thioxo-thiazolidin-4-one, (5Z)-5-[[1-(4-fluorophenyl)pyrazol-4-yl]methylene]-2-thioxo-thiazolidin-4-one, (5Z)-5-[[1-(2-chlorophenyl)pyrazol-4-yl]methylene]-2-thioxo-thiazolidin-4-one, (5Z)-5-[[1-(2-chlorophenyl)pyrazol-4-yl]methylene]-3-methyl-2-thioxo-thiazolidin-4-one, (5Z)-5-[[1-(2-chlorophenyl)pyrazol-4-yl]methylene]-3-ethyl-2-thioxo-thiazolidin-4-one, (5Z)-3-allyl-5-[[1-(2-chlorophenyl)pyrazol-4-yl]methylene]-2-thioxo-thiazolidin-4-one, (5Z)-5-[[1-(3-chlorophenyl)pyrazol-4-yl]methylene]-2-thioxo-thiazolidin-4-one, (5Z)-5-[[1-(3-chlorophenyl)pyrazol-4-yl]methylene]-3-methyl-2-thioxo-thiazolidin-4-one, (5Z)-5-[[1-(3-chlorophenyl)pyrazol-4-yl]methylene]-3-ethyl-2-thioxo-thiazolidin-4-one, (5Z)-3-allyl-5-[[1-(3-chlorophenyl)pyrazol-4-yl]methylene]-2-thioxo-thiazolidin-4-one, (5Z)-5-[[1-(4-chlorophenyl)pyrazol-4-yl]methylene]-2-thioxo-thiazolidin-4-one, (5Z)-5-[[1-(4-chlorophenyl)pyrazol-4-yl]methylene]-3-methyl-2-thioxo-thiazolidin-4-one, (5Z)-5-[[1-(4-chlorophenyl)pyrazol-4-yl]methylene]-3-ethyl-2-thioxo-thiazolidin-4-one, (5Z)-5-[[1-(p-tolyl)pyrazol-4-yl]methylene]-2-thioxo-thiazolidin-4-one, (5Z)-3-methyl-5-[[1-(p-tolyl)pyrazol-4-yl]methylene]-2-thioxo-thiazolidin-4-one, (5Z)-3-ethyl-5-[[1-(p-tolyl)pyrazol-4-yl]methylene]-2-thioxo-thiazolidin-4-one, (5Z)-3-allyl-5-[[1-(p-tolyl)pyrazol-4-yl]methylene]-2-thioxo-thiazolidin-4-one, (5Z)-5-[[1-(4-isopropylphenyl)pyrazol-4-yl]methylene]-2-thioxo-thiazolidin-4-one, (5Z)-3-ethyl-5-[[1-(4-isopropylphenyl)pyrazol-4-yl]methylene]-2-thioxo-thiazolidin-4-one, (5Z)-5-[[1-(4-butylphenyl)pyrazol-4-yl]methylene]-2-thioxo-thiazolidin-4-one, (5Z)-5-[[1-(4-butylphenyl)pyrazol-4-yl]methylene]-3-ethyl-2-thioxo-thiazolidin-4-one, (5Z)-5-[[1-(3,4-dimethylphenyl)pyrazol-4-yl]methylene]-2-thioxo-thiazolidin-4-one, (5Z)-5-[[1-(3,4-dimethylphenyl)pyrazol-4-yl]methylene]-3-ethyl-2-thioxo-thiazolidin-4-one, (5Z)-5-[[1-(2-methoxyphenyl)pyrazol-4-yl]methylene]-2-thioxo-thiazolidin-4-one, (5Z)-5-[[1-(2-naphthyl)pyrazol-4-yl]methylene]-2-thioxo-thiazolidin-4-one, (5Z)-3-ethyl-5-[[1-(2-naphthyl)pyrazol-4-yl]methylene]-2-thioxo-thiazolidin-4-one, (5Z)-5-[[1-(2-pyridyl)pyrazol-4-yl]methylene]-2-thioxo-thiazolidin-4-one, (5Z)-3-(2-hydroxyethyl)-5-[[1-(2-pyridyl)pyrazol-4-yl]methylene]-2-thioxo-thiazolidin-4-one, (5Z)-5-[[1-(3-pyridyl)pyrazol-4-yl]methylene]-2-thioxo-thiazolidin-4-one, (5Z)-3-(2-hydroxyethyl)-5-[[1-(3-pyridyl)pyrazol-4-yl]methylene]-2-thioxo-thiazolidin-4-one, (5Z)-5-[(5-methyl-1-phenyl-pyrazol-4-yl)methylene]-2-thioxo-thiazolidin-4-one, (5Z)-5-[(3,5-dimethyl-1-phenyl-pyrazol-4-yl)methylene]-2-thioxo-thiazolidin-4-one, (5Z)-5-[(l-phenylpyrazol-4-yl)methylene]thiazolidine-2,4-dione, (5Z)-5-[[1-(2-fluorophenyl)pyrazol-4-yl]methylene]thiazolidine- 2,4-dione, (5Z)-5-[[1I-(3-fluorophenyl)pyrazol-4-yl]methylene]thiazolidine-2,4-dione, (5Z)-5-[[1-(4-fluorophenyl)pyrazol-4-yl]methylene]thiazolidine-2,4-dione, (5Z)-5-[[1-(2-chlorophenyl)pyrazol-4-yl]methylene]thiazolidine-2,4-dione, (5Z)-5-[[1-(3-chlorophenyl)pyrazol-4-yl]methylene]thiazolidine-2,4-dione, (5Z)-5-[[1-(4-chlorophenyl)pyrazol-4-yl]methylene]thiazolidine-2,4-dione, (5Z)-5-[[1-(p-tolyl)pyrazol-4-yl]methylene]thiazolidine-2,4-dione, (5Z)-5-[[1-(4-isopropylphenyl)pyrazol-4-yl]methylene]thiazolidine-2,4-dione, (5Z)-5-[[1-(4-butylphenyl)pyrazol-4-yl]methylene]thiazolidine-2,4-dione, (5Z)-5-[[1-(3,4-dimethylphenyl)pyrazol-4-yl]methylene]thiazolidine-2,4-dione, (5Z)-5-[[1-(2-methoxyphenyl)pyrazol-4-yl]methylene]thiazolidine-2,4-dione, (5Z)-5-[[1-(2-naphthyl)pyrazol-4-yl]methylene]thiazolidine-2,4-dione, (5Z)-5-[[1-(3-pyridyl)pyrazol-4-yl]methylene]thiazolidine-2,4-dione, (5Z)-5-[(3-methyl-1-phenyl-pyrazol-4-yl)methylene]thiazolidine-2,4-dione, (5Z)-5-[(3,5-dimethyl-1-phenyl-pyrazol-4-yl)methylene]thiazolidine-2,4-dione, (5Z)-5-[[1-(4-chlorophenyl)pyrazol-3-yl]methylene]-2-thioxo-thiazolidin-4-one, (5Z)-5-[[1-(2-pyridyl)pyrazol-3-yl]methylene]-2-thioxo-thiazolidin-4-one, (5Z)-5-[[1-(3-pyridyl)pyrazol-3-yl]methylene]-2-thioxo-thiazolidin-4-one, (5Z)-5-[[1-phenylpyrazol-3-yl]methylene]thiazolidine-2,4-dione, (5Z)-5-[[1-(2-pyridyl)pyrazol-3-yl]methylene]thiazolidine-2,4-dione, (5Z)-5-[[1-(3-pyridyl)pyrazol-3-yl]methylene]thiazolidine-2,4-dione and (5Z)-5-[[1-(4-pyridyl)pyrazol-3-yl]methylene]thiazolidine-2,4-dione.

The structural formulas of the compounds listed above are summarized in Table 1 below.

TABLE 1

| 1 | 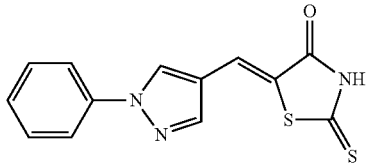 [SMILES: O=C1NC(=S)S/C1=C\c1cnn(-c2ccccc2)c1] | (5Z)-5-[(1-phenylpyrazol-4-yl)methylene]-2-thioxo-thiazolidin-4-one |
| --- | --- | --- |
| 2 | 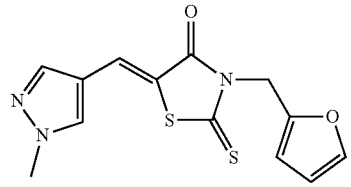 [SMILES: Cn1cc(/C=C2\SC(=S)N(Cc3ccco3)C2=O)cn1] | (5Z)-3-(2-furylmethyl)-5-[(1-methylpyrazol-4-yl)methylene]-2-thioxo-thiazolidin-4-one |
| 3 | 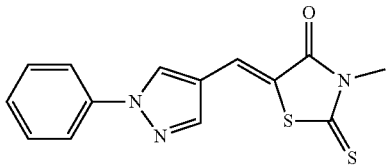 [SMILES: CN1C(=O)/C(=C/c2cnn(-c3ccccc3)c2)SC1=S] | (5Z)-3-methyl-5-[(1-phenylpyrazol-4-yl)methylene]-2-thioxo-thiazolidin-4-one |
| 4 | 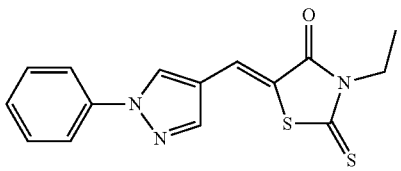 [SMILES: CCN1C(=O)/C(=C/c2cnn(-c3ccccc3)c2)SC1=S] | (5Z)-3-ethyl-5-[(1-phenylpyrazol-4-yl)methylene]-2-thioxo-thiazolidin-4-one |
| 5 | 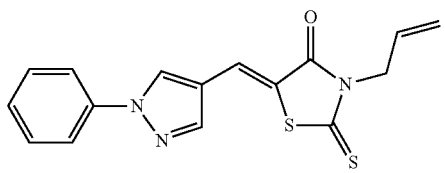 [SMILES: C=CCN1C(=O)/C(=C/c2cnn(-c3ccccc3)c2)SC1=S] | (5Z)-3-allyl-5-[(1-phenylpyrazol-4-yl)methylene]-2-thioxo-thiazolidin-4-one |
| 6 | 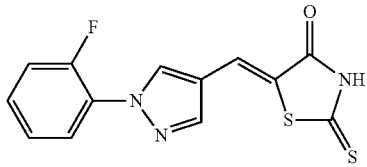 | (5Z)-5-[[1-(2-fluorophenyl)pyrazol-4-yl]methylene]-2-thioxo-thiazolidin-4-one |

TABLE 1-continued

| | | |
|---|---|---|
| 7 | 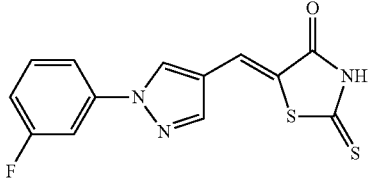 [SMILES: O=C1NC(=S)S/C1=C\c1cnn(-c2cccc(F)c2)c1] | (5Z)-5-[[1-(3-fluorophenyl)pyrazol-4-yl]methylene]-2-thioxo-thiazolidin-4-one |
| 8 | 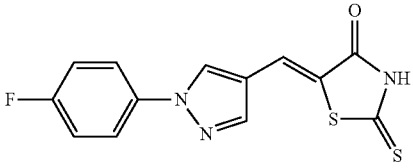 [SMILES: O=C1NC(=S)S/C1=C\c1cnn(-c2ccc(F)cc2)c1] | (5Z)-5-[[1-(4-fluorophenyl)pyrazol-4-yl]methylene]-2-thioxo-thiazolidin-4-one |
| 9 | 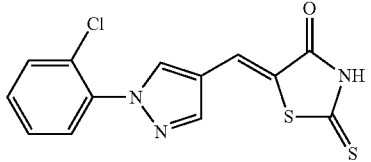 [SMILES: O=C1NC(=S)S/C1=C\c1cnn(-c2ccccc2Cl)c1] | (5Z)-5-[[1-(2-chlorophenyl)pyrazol-4-yl]methylene]-2-thioxo-thiazolidin-4-one |
| 10 | 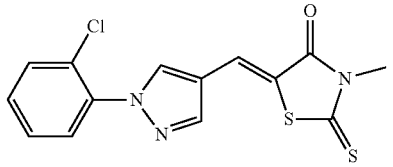 [SMILES: CN1C(=O)/C(=C/c2cnn(-c3ccccc3Cl)c2)SC1=S] | (5Z)-5-[[1-(2-chlorophenyl)pyrazol-4-yl]methylene]-3-methyl-2-thioxo-thiazolidin-4-one |
| 11 | 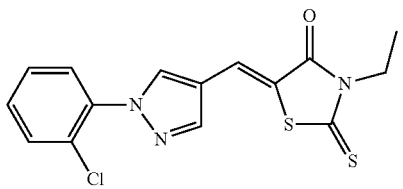 [SMILES: CCN1C(=O)/C(=C/c2cnn(-c3ccccc3Cl)c2)SC1=S] | (5Z)-5-[[1-(2-chlorophenyl)pyrazol-4-yl]methylene]-3-ethyl-2-thioxo-thiazolidin-4-one |
| 12 | 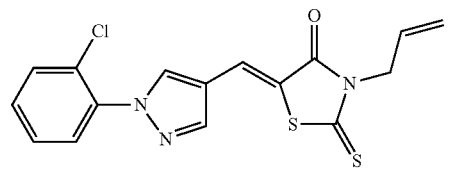 [SMILES: C=CCN1C(=O)/C(=C/c2cnn(-c3ccccc3Cl)c2)SC1=S] | (5Z)-3-allyl-5-[[1-(2-chlorophenyl)pyrazol-4-yl]methylene]-2-thioxo-thiazolidin-4-one |
| 13 | 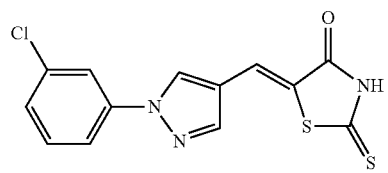 [SMILES: O=C1NC(=S)S/C1=C\c1cnn(-c2cccc(Cl)c2)c1] | (5Z)-5-[[1-(3-chlorophenyl)pyrazol-4-yl]methylene]-2-thioxo-thiazolidin-4-one |
| 14 | 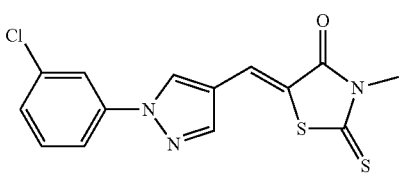 [SMILES: CN1C(=O)/C(=C/c2cnn(-c3cccc(Cl)c3)c2)SC1=S] | (5Z)-5-[[1-(3-chlorophenyl)pyrazol-4-yl]methylene]-3-methyl-2-thioxo-thiazolidin-4-one |

TABLE 1-continued

| | | |
|---|---|---|
| 15 | | (5Z)-5-[[1-(3-chlorophenyl)pyrazol-4-yl]methylene]-3-ethyl-2-thioxo-thiazolidin-4-one |
| 16 | | (5Z)-3-allyl-5-[[1-(3-chlorophenyl)pyrazol-4-yl]methylene]-2-thioxo-thiazolidin-4-one |
| 17 | | (5Z)-5-[[1-(4-chlorophenyl)pyrazol-4-yl]methylene]-2-thioxo-thiazolidin-4-one |
| 18 | | (5Z)-5-[[1-(4-chlorophenyl)pyrazol-4-yl]methylene-3-methyl-2-thioxo-thiazolidin-4-one |
| 19 | | (5Z)-5-[[1-(4-chlorophenyl)pyrazol-4-yl]methylene]-3-ethyl-2-thioxo-thiazolidin-4-one |
| 20 | | (5Z)-5-[[1-(p-tolyl)pyrazol-4-yl]methylene]-2-thioxo-thiazolidin-4-one |
| 21 | | (5Z)-3-methyl-5-[[1-(p-tolyl)pyrazol-4-yl]methylene]-2-thioxo-thiazolidin-4-one |
| 22 | | (5Z)-3-ethyl-5-[[1-(p-tolyl)pyrazol-4-yl]methylene]-2-thioxo-thiazolidin-4-one |
| 23 | | (5Z)-3-allyl-5-[[1-(p-tolyl)pyrazol-4-yl]methylene]-2-thioxo-thiazolidin-4-one |

TABLE 1-continued

| # | Structure | Name |
|---|---|---|
| 24 | 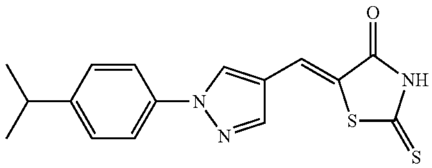 [SMILES: CC(C)c1ccc(-n2cc(/C=C3\SC(=S)NC3=O)cn2)cc1] | (5Z)-5-[[1-(4-isopropylphenyl)pyrazol-4-yl]methylene]-2-thioxo-thiazolidin-4-one |
| 25 | 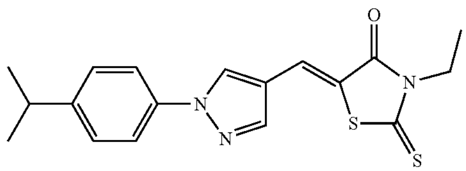 [SMILES: CCN1C(=O)/C(=C/c2cnn(-c3ccc(C(C)C)cc3)c2)SC1=S] | (5Z)-3-ethyl-5-[[1-(4-isopropylphenyl)pyrazol-4-yl]methylene]-2-thioxo-thiazolidin-4-one |
| 26 | 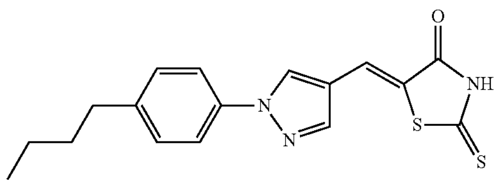 [SMILES: CCCCc1ccc(-n2cc(/C=C3\SC(=S)NC3=O)cn2)cc1] | (5Z)-5-[[1-(4-butylphenyl)pyrazol-4-yl]methylene]-2-thioxo-thiazolidin-4-one |
| 27 | 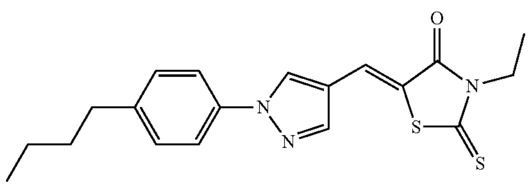 [SMILES: CCCCc1ccc(-n2cc(/C=C3\SC(=S)N(CC)C3=O)cn2)cc1] | (5Z)-5-[[1-(4-butylphenyl)pyrazol-4-yl]methylene]-3-ethyl-2-thioxo-thiazolidin-4-one |
| 28 | 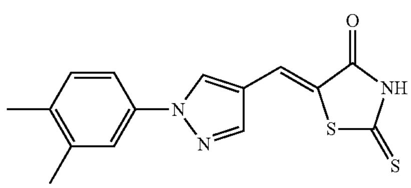 [SMILES: Cc1ccc(-n2cc(/C=C3\SC(=S)NC3=O)cn2)cc1C] | (5Z)-5-[[1-(3,4-dimethylphenyl)pyrazol-4-yl]methylene]-2-thioxo-thiazolidin-4-one |
| 29 | 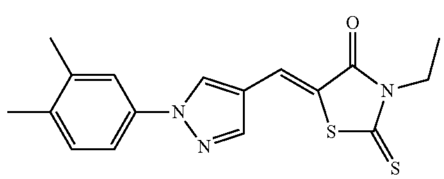 [SMILES: CCN1C(=O)/C(=C/c2cnn(-c3ccc(C)c(C)c3)c2)SC1=S] | (5Z)-5-[[1-(3,4-dimethylphenyl)pyrazol-4-yl]methylene]-3-ethyl-2-thioxo-thiazolidin-4-one |
| 30 | 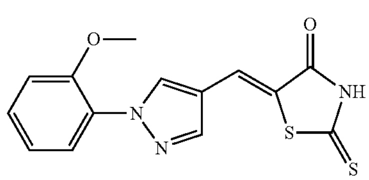 [SMILES: COc1ccccc1-n1cc(/C=C2\SC(=S)NC2=O)cn1] | (5Z)-5-[[1-(2-methoxyphenyl)pyrazol-4-yl]methylene]-2-thioxo-thiazolidin-4-one |
| 31 | 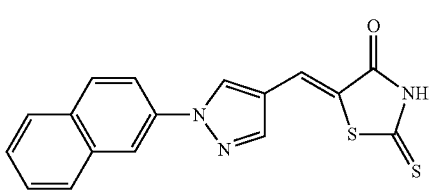 | (5Z)-5-[[1-(2-naphthyl)pyrazol-4-yl]methylene]-2-thioxo-thiazolidin-4-one |
| 32 | 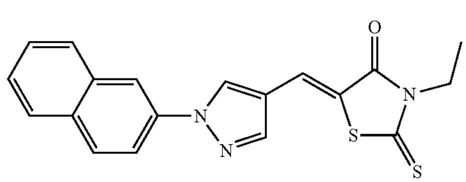 [SMILES: CCN1C(=O)/C(=C/c2cnn(-c3ccc4ccccc4c3)c2)SC1=S] | (5Z)-3-ethyl-5-[[1-(2-naphthyl)pyrazol-4-yl]methylene]-2-thioxo-thiazolidin-4-one |

TABLE 1-continued

| | | |
|---|---|---|
| 33 | | (5Z)-5-[[1-(2-pyridiyl)pyrazol-4-yl]methylene]-2-thioxo-thiazolidin-4-one |
| 34 | | (5Z)-3-(2-hydroxyethyl)-5-[[1-(2-pyridyl)pyrazol-4-yl]methylene]-2-thioxo-thiazolidin-4-one |
| 35 | | (5Z)-5-[[1-(3-pyridyl)pyrazol-4-yl]methylene]-2-thioxo-thiazolidin-4-one |
| 36 | | (5Z)-3-(2-hydroxyethyl)-5-[[1-(3-pyridyl)pyrazol-4-yl]methylene]-2-thioxo-thiazolidin-4-one |
| 37 | | (5Z)-5-[(5-methyl-1-phenyl-pyrazol-4-yl)methylene]-2-thioxo-thiazolidin-4-one |
| 38 | | (5Z)-5-[(3,5-dimethyl-1-phenyl-pyrazol-4-yl)methylene]-2-thioxo-thiazodin-4-one |
| 39 | | (5Z)-5-[(1-phenylpyrazol-4-yl)methylene]thiazolidine-2,4-dione |
| 40 | | (5Z)-5-[[1-(2-fluorophenyl)pyrazol-4-yl]methylene]thiazolidine-2,4-dione |
| 41 | | (5Z)-5-[[1-(3-fluorophenyl)pyrazol-4-yl]methylene]thiazolidine-2,4-dione |

TABLE 1-continued

| | | |
|---|---|---|
| 42 | 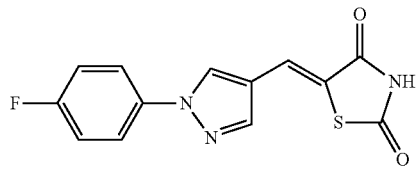 | (5Z)-5-[[1-(4-fluorophenyl)pyrazol-4-yl]methylene]thiazolidine-2,4-dione |
| 43 | 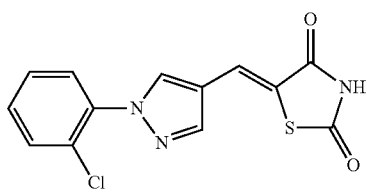 | (5Z)-5-[[1-(2-chlorophenyl)pyrazol-4-yl]methylene]thiazolidine-2,4-dione |
| 44 | 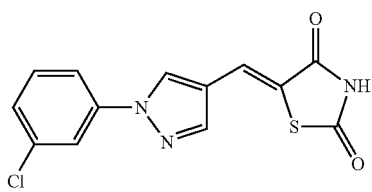 [SMILES: O=C1NC(=O)/C(=C/c2cnn(-c3cccc(F)c3)c2)S1] | (5Z)-5-[[1-(3-chlorophenyl)pyrazol-4-yl]methylene]thiazolidine-2,4-dione |
| 45 | 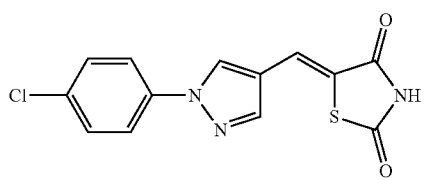 [SMILES: O=C1NC(=O)/C(=C/c2cnn(-c3ccc(Cl)cc3)c2)S1] | (5Z)-5-[[1-(4-chlorophenyl)pyrazol-4-yl]methylene]thiazolidine-2,4-dione |
| 46 | 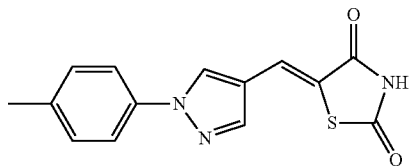 [SMILES: Cc1ccc(-n2cc(/C=C3\SC(=O)NC3=O)cn2)cc1] | (5Z)-5-[[1-(p-tolyl)pyrazol-4-yl]methylene]thiazolidine-2,4-dione |
| 47 | 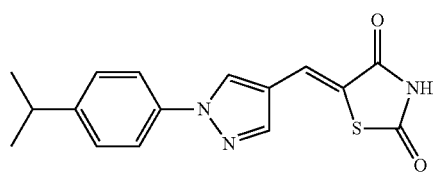 [SMILES: CC(C)c1ccc(-n2cc(/C=C3\SC(=O)NC3=O)cn2)cc1] | (5Z)-5-[[1-(4-isopropylphenyl)pyrazol-4-yl]methylene]thiazolidine-2,4-dione |
| 48 | 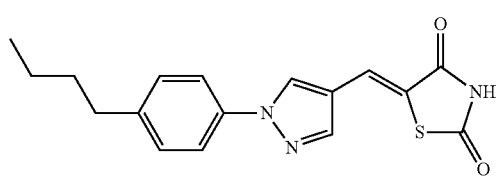 [SMILES: CCCCc1ccc(-n2cc(/C=C3\SC(=O)NC3=O)cn2)cc1] | (5Z)-5-[[1-(4-butylphenyl)pyrazol-4-yl]methylene]thiazolidine-2,4-dione |
| 49 | 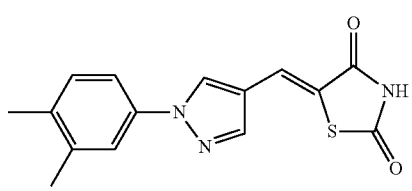 [SMILES: Cc1ccc(-n2cc(/C=C3\SC(=O)NC3=O)cn2)cc1C] | (5Z)-5-[[1-(3,4-dimethylphenyl)pyrazol-4-yl]methylene]thiazolidine-2,4-dione |

TABLE 1-continued

| | | |
|---|---|---|
| 50 | 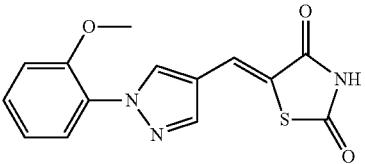 [SMILES: COc1ccccc1-n1cc(/C=C2\SC(=O)NC2=O)cn1] | (5Z)-5-[[1-(2-methoxyphenyl)pyrazol-4-yl]methylene]thiazolidine-2,4-dione |
| 51 | 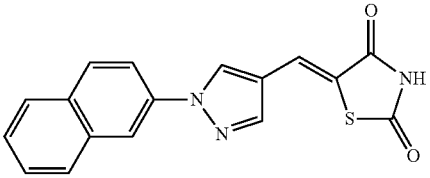 | (5Z)-5-[[1-(2-naphthyl)pyrazol-4-yl]methylene]thiazolidine-2,4-dione |
| 52 | 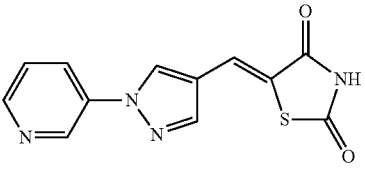 [SMILES: O=C1NC(=O)/C(=C/c2cnn(-c3cccnc3)c2)S1] | (5Z)-5-[[1-(3-pyridyl)pyrazol-4-yl]methylene]thiazolidine-2,4-dione |
| 53 | 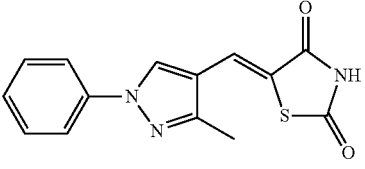 [SMILES: Cc1nn(-c2ccccc2)cc1/C=C1\SC(=O)NC1=O] | (5Z)-5-[(3-methyl-1-phenyl-pyrazol-4-yl)methylene]thiazolidine-2,4-dione |
| 54 | 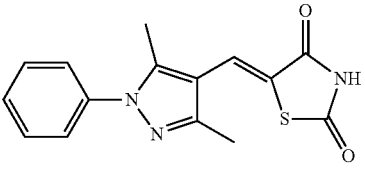 | (5Z)-5-[(3,5-dimethyl-1-phenyl-pyrazol-4-yl]methylene]thiazolidine-2,4-dione |
| 55 | 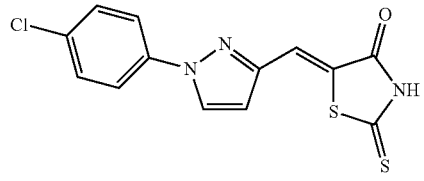 [SMILES: O=C1NC(=S)S/C1=C\c1ccn(-c2ccc(Cl)cc2)n1] | (5Z)-5-[[1-(4-chlorophenyl)pyrazol-3-yl]methylene]-2-thioxo-thiazolidin-4-one |
| 56 | 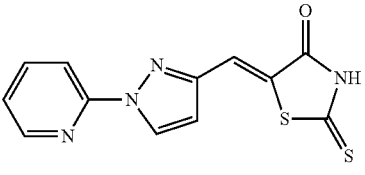 [SMILES: O=C1NC(=S)S/C1=C\c1ccn(-c2ccccn2)n1] | (5Z)-5-[[1-(2-pyridyl)pyrazol-3-yl]methylene]-2-thioxo-thiazolidin-4-one |
| 57 | 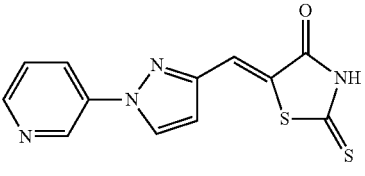 [SMILES: O=C1NC(=S)S/C1=C\c1ccn(-c2cccnc2)n1] | (5Z)-5-[[1-(3-pyridyl)pyrazol-3-yl]methylene]-2-thioxo-thiazolidin-4-one |
| 58 | 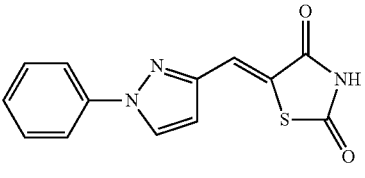 [SMILES: O=C1NC(=O)/C(=C/c2ccn(-c3ccccc3)n2)S1] | (5Z)-5-[[1-phenylpyrazol-3-yl]methylene]thiazolidine-2,4-dione |

TABLE 1-continued

| 59 | | (5Z)-5-[[1-(2-pyridyl)pyrazol-3-yl]methylene]thiazolidine-2,4-dione |
| 60 | | (5Z)-5-[[1-(3-pyridyl)pyrazol-3-yl]methylene]thiazolidine-2,4-dione |
| 61 | | (5Z)-5-[[1-(4-pyridyl)pyrazol-3-yl]methylene]thiazolidine-2,4-dione |

The compound of Formula 1 of the present invention can be used in the form of a pharmaceutically acceptable salt. As the salt, an acid addition salt formed with various organic or inorganic acids with which are pharmaceutically or physiologically acceptable is useful. Some organic acids can suitably be used, for example, carboxylic acid, phosphonic acid, sulfonic acid, acetic acid, propionic acid, octanoic acid, decanoic acid, glycolic acid, lactic acid, fumaric acid, succinic acid, adipic acid, malic acid, tartaric acid, citric acid, glutamic acid, aspartic acid, maleic acid, benzoic acid, salicylic acid, phthalic acid, phenylacetic acid, benzenesulfonic acid, 2-naphthalenesulfonic acid, methyl sulfuric acid, ethyl sulfuric acid, dodecyl sulfuric acid or the like. Some inorganic acids can suitably be used, for example, hydrochloric acid, sulfuric acid or phosphoric acid.

The compound of Formula 1 of the present invention may include not only pharmaceutically acceptable salts, but also all salts, hydrates and solvates, racemates, or stereoisomers that can be prepared by conventional methods.

The present invention also provides a method for preparing the compound of claim 1 or a pharmaceutically acceptable salt thereof, prepared by the following Reaction Formula:

[Reaction Formula 1]

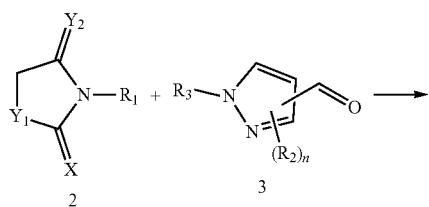

-continued

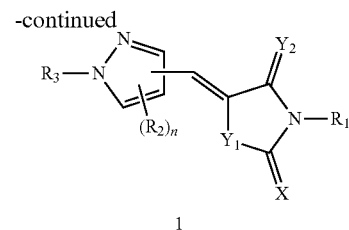

In Reaction Formula 1 described above,

R1, R2, R3, X, Y1, Y2 and n are as defined in claim 1.

In the production method of the present invention, the reaction described above may be carried out by mixing and heating Compound 2 and Compound 3 in the presence or absence of a solvent with the presence of Lewis or a photoacid catalyst.

The useful catalysts, for example, are HCl, HBr, H2SO4, acetic acid, trifluoroic acid, p-toluenesulfonic acid, trimethylsilylchloride, trimethylsilyliodide, boron trifluoride etherate, copper(I) chloride, iron(III) chloride. indium (III) chloride, ytterbium triflate, cerium (III) chloride, zirconium (IV) chloride, zirconium oxychloride (IV), lithium bromide, phenylpyruvate, calcium chloride, polyphosphate esters, or solid clay acid catalysts such as Montmorillonite KSF clay or combinations of these catalysts.

Useful solvents may preferably include polar solvents such as acetonitrile, acetic acid, methanol, ethanol, or other alcohols, tetrahydrofuran, dimethylformamide, dimethylacetamide, N-methylpyrrolidone or dioxane.

Heating can be done under conventional heating conditions or microwave conditions. Useful solvents may preferably include polar solvents such as acetonitrile, acetic acid, methanol, ethanol, or other alcohols, tetrahydrofuran, dimethylformamide, dimethylacetamide, N-methylpyrrolidone or dioxane.

Heating can be done under conventional heating conditions or microwave conditions.

Preferably, the preparation method described above according to the present invention can be applied with both the Compound 2 and the Compound 3 for conventional condensation reaction to produce the compound of Formula 1. For example, the compound of Formula 1 can be produced by a knoevenagel condensation reaction in which sodium acetate is added to the Compound 2 and the Compound 3 in an organic solvent and stirred for 10 to 20 hours at 50 to 80° C.

The product produced according to scheme 1 can be purified with additional steps such as washing, concentration, ethyl acetate extraction, drying and column chromatography and the like, and its structural and physicochemical traits can be analyzed by IR, NMR, melting point (mp) measurement and the like.

Meanwhile, in Reaction Formula 1, Compound 2 and Compound 3 may be used commercially available compounds, respectively, or, for example, Compound 2 may be synthesized according to Reaction Formula 2 below, and Compound 3 may be synthesized according to Reaction Formula 3 below:

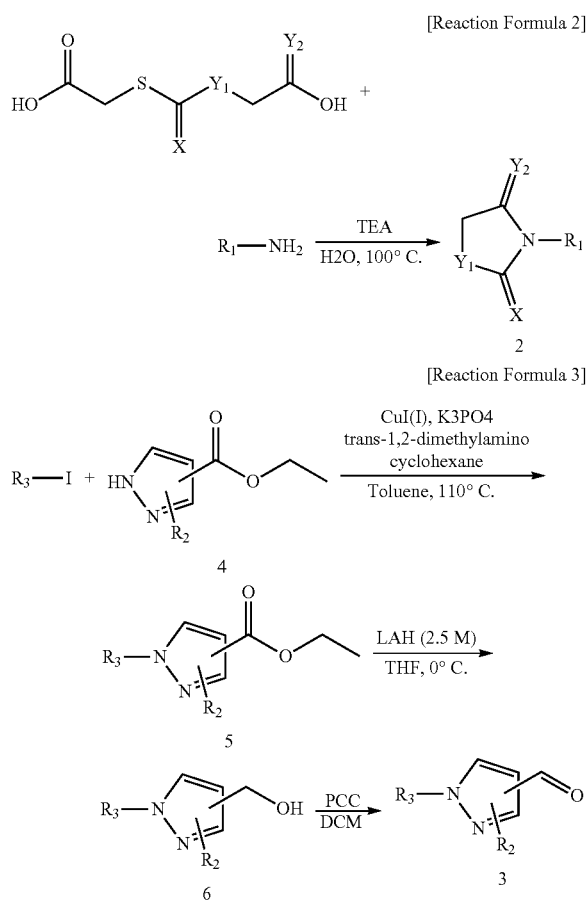

In Reaction Formula 2 and 3 above, $R_1$, $R_2$, $R_3$, X, $Y_1$, $Y_2$ and n are as defined in claim 1.

Meanwhile, according to an embodiment of the present invention, it was confirmed that the compound of Formula 1 or a pharmaceutically acceptable salt thereof inhibits the binding of LRS and RagD, thereby inhibiting the activity of mTORC1.

mTOR is known to be involved in a variety of physiological and pathological signaling pathways, and it has been reported that it may be an important target for epilepsy treatment as it is particularly closely related to the process of epileptogenesis (Pharmacological Reports, vol 67, issue 3, 636-646).

Leucyl tRNA synthetase (LRS) functions as a key factor for amino acid signaling to mTORC1. That is, LRS directly binds to Rag GTPase, an amino acid-dependent signaling mediator to mTORC1, and acts as a GTPase-activating protein (GAP) for Rag GTPase, so that Rag GTPase activates mTORC1. In addition, leucyl tRNA synthetase (LRS) plays an important role in the activation of mTORC1 mediated by amino acids, so that LRS detects the concentration of leucine in cells and affects the activation of mTORC1 mediated by leucine. Rag protein belongs to the Rag subfamily among Ras small GTPases, and there are four types of RagA, RagB, RagC, and RagD. Among them, A and B are the orthologs of yeast Gtr1p GTPase, and C and D are the orthologs of yeast Gtr2p. RagD binds with A or B to form a dimer and mediates mTORC1 activity by amino acids. (Trends in Biochemical Sciences, 33: 565-568, 2008). Therefore, inhibition of the binding between LRS and RagD inhibits the activation of mTORC1, which may result in an effect of treating brain diseases related to the mTOR pathway.

On the other hand, autophagy, or intracellular self-digestion, is a cellular pathway associated with protein and organelle degradation, and are closely relevant to human disease and physiology. For example, dysfunction of autophagy is associated with cancer, neurodegeneration, microbial transmission and aging. Paradoxically, while autophagy is a major protective process for cells, it may also play a role in cell death in cancer cells.

However, mTOR is the main negative control factor of autophagy. Direct inhibitors of mTOR and inhibitors of the factors that activates mTOR can then induce autophagosis. mTOR kinase regulates cell growth and autophagy in response to growth factor and nutrient levels. Consequently, autophagy protects the cells from damage that leads to neurodegeneration. Autophagy, a major degradation pathway for organelles and long-lived proteins, is essential for the survival of neurons. According to the prior report, as a cause of some major neurodegenerative diseases such as Alzheimer's disease, Huntington's disease, Parkinson's disease, autophagy defects have been suggested. The findings in these studies indicate that autophagosis is altered in the early stages of the disease, and that the dysfunction of autophagosis plays an important role in the pathological progression of neurodegenerative brain diseases such as Alzheimer's disease, Huntington's disease, and Parkinson's disease.

In addition, the mTOR pathway is known to be closely related to the occurrence of depression. A decrease in mTOR signaling was confirmed in a study using an animal model of depression. In particular, a change in mTOR signaling was observed in a study using a chronic unpredictable stress (CUS) model that induces changes similar to neurobiochemical changes occurring in depressed patients. Long-term CUS is known to cause impaired reward salience in rodents, similar to loss of pleasure, a symptom of depressed patients. The depressive behavior observed in rodents exposed to CUS is known to be associated with a decrease in phosphorylated mTOR in the anterior prefrontal lobe, hippocampus and amygdala and a decrease in the degree of phosphorylation of p70S6K, a sub-element of mTOR signaling. And in mice with removal of mTOR gene, a behavior similar to that of depressive behavior caused by CUS has been observed. (Neurosci Biobehav Rev 2012; 36:2085-2117, J Psychiatry Neurosci 2013; 38:306-316., Prog Neuropsychopharmacol Biol Psychiatry 2013; 40:240-245.)

Therefore, the pathologic mechanisms of neurodegenerative brain diseases such as Alzheimer's disease, Parkinson's disease, Huntington's disease and depression are also related to the mTOR pathway (Bov'e et al. (2011) Nature Reviews Neuroscience 12, 437-452), and mTOR inhibitors may be therapeutic targets for these brain diseases.

Other brain diseases related to dysfunction of the mTOR signaling system include Tuberous sclerosis, Autism spectrum disorder, Cowden syndrome, and Bannayan-Riley-Ruvacalba syndrome, Lhermitte-Duclos disease, Neurofibromatosis, Neurofibromatosis type 1, Autism, Nonsyndromic autism, Schizophrenia (Neuron 84, Oct. 22, 2014).

Accordingly, the present invention provides a pharmaceutical composition for preventing or treating brain diseases related to the mTOR pathway, comprising the compound of Formula 1 or a pharmaceutically acceptable salt thereof as an active ingredient.

In addition, the present invention provides a pharmaceutical composition for preventing or treating brain diseases related to mTOR pathway, consisting of the compound of Formula 1 or a pharmaceutically acceptable salt thereof as an active ingredient.

In addition, the present invention provides a pharmaceutical composition for preventing or treating brain diseases related to the mTOR pathway, consisting essentially of the compound of Formula 1 or a pharmaceutically acceptable salt thereof as an active ingredient.

According to an embodiment of the present invention, in addition to the effect of inhibiting the activity of mTOR by inhibiting the binding of LRS and RagD, the compound of the present invention appears to have very high blood-brain barrier (BBB) permeability, and acts directly on the brain Thus, it was confirmed that it can exhibit excellent effects in the treatment of brain diseases.

In the present invention, the brain disease related to mTOR pathway may preferably be a brain disease related to the mTOR complex 1 (mTORC1) pathway. More preferably the brain disease can be a disease selected from the group consisting of epilepsy, Alzheimer's disease, Parkinson's disease, depression, Huntington's disease, tuberous sclerosis, Autism spectrum disorder, Cowden syndrome, Bannayan-Riley-Ruvacalba syndrome, Lhermitte-Duclos disease, Neurofibromatosis, Neurofibromatosis type 1, autism, nonsyndromic autism, and schizophrenia, and most preferably, the brain disease can be epilepsy.

The pharmaceutical composition according to the present invention may contain the compound of Formula 1 or a pharmaceutically acceptable salt thereof alone, or may further contain one or more pharmaceutically acceptable carriers, excipients, or diluents.

The pharmaceutically acceptable carrier may further include, for example, a carrier for oral administration or a carrier for parenteral administration. Carriers for oral administration may include lactose, starch, cellulose derivatives, magnesium stearate, stearic acid, and the like. In addition, the carrier for parenteral administration may include water, suitable oil, saline, aqueous glucose and glycol, and the like, and may further include stabilizers and preservatives. Suitable stabilizers may be antioxidants such as sodium hydrogen sulfite, sodium sulfite or ascorbic acid. Suitable preservatives may be benzalkonium chloride, methyl- or propyl-paraben and chlorobutanol. Other pharmaceutically acceptable carriers may refer to those known in the art.

The pharmaceutical composition of the present invention can be administered to mammals including humans by any method. For example, it can be administered orally or parenterally. Parenteral administration methods include, but are not limited to, intravenous, intramuscular, intraarterial, intramedullary, intrathecal, intracardiac, transdermal, subcutaneous, intraperitoneal, intranasal, intestinal, topical, sublingual or rectal administration. For example, the phanmaceutical composition of the present invention may be prepared in an injectable formulation and administered by a method of lightly pricking the skin with a 30 gauge thin injection needle, or by applying it directly to the skin.

The pharmaceutical composition of the present invention can be formulated into a formulation for oral administration or parenteral administration according to the route of administration as described above.

In the case of a formulation for oral administration, the composition of the present invention may be formulated using a method known in the art such as a powder, granule, tablet, pill, dragee (sugar coating tablet), capsule, liquid, gel, syrup, slurry, suspension. For example, in oral preparations, tablets or dragees can be obtained by blending the active ingredient with a solid excipient, pulverizing it, adding a suitable auxiliary, and processing into a granule mixture. Examples of suitable excipients include sugars including lactose, dextrose, sucrose, sorbitol, mannitol, xylitol, erythritol and maltitol, starches including corn starch, wheat starch, rice starch and potato starch, celluloses including methyl cellulose, sodium carboxymethylcellulose and hydroxypropylmethyl-cellulose, and fillers including gelatin and polyvinylpyrrolidone. In addition, in some cases, crosslinked polyvinylpyrrolidone, agar, alginic acid or sodium alginate may be added as a disintegrant. Furthermore, the pharmaceutical composition of the present invention may further include an anti-aggregating agent, a lubricant, a wetting agent, a flavoring agent, an emulsifying agent and a preservative.

In the case of a formulation for parenteral administration, it can be formulated in the form of injections, creams, lotions, ointments for external use, oils, moisturizers, gels, aerosols, and nasal inhalants by methods known in the art. These formulations are described in formulas generally known to all pharmaceutical chemistry.

The total effective dose of the pharmaceutical composition of the present invention may be administered to a patient in a single dose, or may be administered to the subject in a multiple dose for a long period of time according to a fractionated treatment protocol. In the pharmaceutical composition of the present invention, the content of the active ingredient may vary depending on the severity of disease. Preferably, the pharmaceutical composition of the present invention may be administered in an amount of 0.01 ug to 1,000 mg, more preferably 0.1 ug to 100 mg per 1 kg of body weight per day. However, the effective dose of the pharmaceutical composition of the present invention is determined by considering various factors including the age, body weight, health conditions, and gender of the patient, the severity of disease, diet, and excretion rate, in addition to an administration route and the number of treatment times of the pharmaceutical composition. Accordingly, considering such an aspect, those skilled in the art may determine an effective dose of the pharmaceutical composition of the present invention suitable for a specific use for preventing and treating neurodegenerative disease. So long as the pharmaceutical composition of the present invention exhibits the effects of the present invention, formulations thereof, routes of administration, and methods of administration are not particularly limited.

In the present invention, the 'treatment' refers generically to improving the symptoms of brain diseases related to the mTOR pathway, which preferably cures, substantially prevents, or improves the condition of epilepsy, Alzheimer's disease, Parkinson's disease, Huntington's disease, etc. It may include, but is not limited to, alleviating, curing, or preventing one symptom or most of the symptoms resulting from these brain diseases.

The present invention provides the use of the compound of Chemical Formula 1 or a pharmaceutically acceptable salt thereof for the preparation of an agent for preventing or treating a brain disease associated with mTOR (mechanistic target of rapamycin) pathway.

The present invention provides the method for treating a brain disease associated with mTOR pathway in a subject in need thereof, the method comprising administering an effective amount of a composition comprising the compound of Chemical Formula 1 or a pharmaceutically acceptable salt thereof as an active ingredient to the subject in need thereof The term 'effective amount' of the present invention means an amount which exhibits an effect of improving, treating, preventing, detecting, diagnosing, or inhibiting or reducing brain diseases associated with mTOR pathway when administered to the subject. The 'subject' may be animals, preferably, mammals, particularly animals including humans and may also be cells, tissues, and organs derived from animals. The subject may be a patient requiring the effects.

In the present invention, the term 'comprising' is used in the same way as 'containing' or 'characteristic', and does not exclude additional component elements or method steps not mentioned in the composition or method. The term 'consisting of' means to exclude additional elements, steps, or components, which are not separately described. The term "essentially consisting of" means in the scope of the composition or method, including the component elements or steps described, as well as the component elements or steps that do not substantially affect their basic properties.

Effect of the Invention

The compound represented by Chemical Formula 1 according to the present invention has an excellent effect of inhibiting mTORC1 and has excellent blood-brain barrier permeability, and can be very useful in preventing or treating brain diseases associated with mTOR pathway.

BRIEF DESCRIPTION OF DRAWINGS

The patent or application file contains at least one drawing executed in color. Copies of this patent or patent application publication with color drawing(s) will be provided by the Office upon request and payment of the necessary fee.

MODE FOR CARRYING OUT INVENTION

Figure 1A:
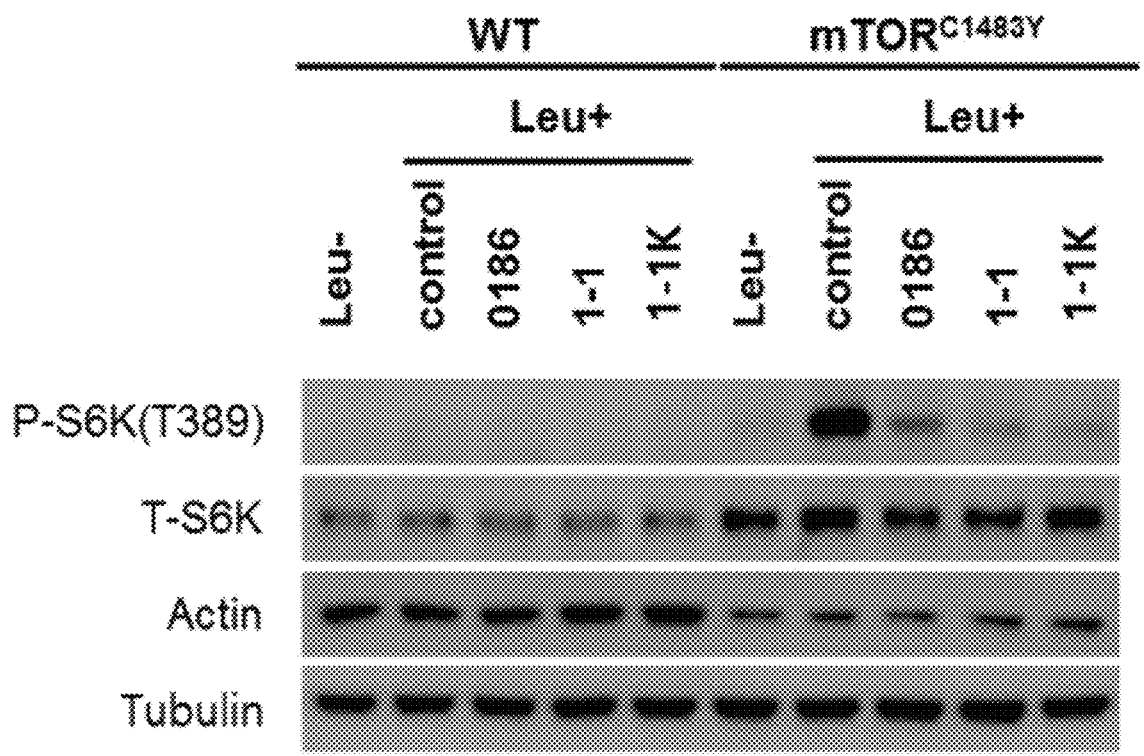
FIGS. 1A and 1B show the immunoblot results (A) of S6K phosphorylation after treatment with the compound of Example 1-1 or a salt thereof to NIH3T3 cells bearing mTOR C1483Y mutation and a graph (B) showing quantification thereof (Leu: leucine).

Hereinafter, the present invention will be described in detail.

However, the following examples are only illustrative of the present invention, and the contents of the present invention are not limited to the following examples.

Example 1: Preparation of Compound

Example 1-0. Preparation of Starting Material

The starting materials to be used in the preparation of the following examples were prepared according to Reaction Formula 2 and Reaction Formula 3.

Specifically, in order to prepare N-substituted rhodanine, amine (1 eq) and triethylamine (1 eq) containing a substituent were added to suspension of 2,2'-[thiocarbonylbis(sulphenidyl)]diacetic acid (1 eq) and water (1 eq), and the mixture was stirred at 100° C. for 20 hours. After completing reaction, the reaction mixture was concentrated under reduced pressure, and was purified by column chromatography (eluent: ethyl acetate/hexane (1:1) mixture) to obtain compound 2 of Chemical Formula 1 (2-30%).

In addition, to prepare N-substituted-pyrazole-3-carbaaldehyde, 1H-pyrazole-3-carboxylate ethyl ester and iodo derivatives (1.05 eq) having various substituents ($R_3$) and copper iodide (cat.), potassium phosphate (2.5 eq) and trans-1,2-dimethylaminocyclohexane (0.2 eq) were added to toluene solution, and the mixture remains to react through a microwave reactor at 110° C. for 2 hours to obtain compound 5 of Reaction Formula 3. In a round bottom flask substituted with argon, the compound 5 was added to anhydrous tetrahydrofuran, and the solution was cooled to 0° C. Lithium aluminum hydride (2.5M solution of tetrahydrofuran, 1.5 eq) was slowly added to reaction solution, followed by stirring at 0° C. for one hour. After completion of the reaction, diethyl ether, distilled water and 15% (wt %)

aqueous sodium hydroxide solution were added to terminate the reaction, and the resulting suspension was filtered and concentrated under reduced pressure to synthesize compound 6 of Reaction Formula 3. Without further purification, it was used in further reaction. Compound 6 was added to pyridinium chlorochromate (3 eq) in dichloromethane solution, followed by stirring for 2 hours at room temperature. After completion of the reaction, a large amount of diethyl ether was added to the reaction suspension, followed by filtering. The obtained filtrate was concentrated under reduced pressure and the concentrate was purified through column chromatography (eluent: ethyl acetate/hexane (1:1) mixture) to obtain compound 3 of Reaction Formula 1.

Example 1-1. Preparation of (5Z)-5-[(1-phenylpyrazol-4-yl)methylene]-2-thioxo-thiazolidin-4-one 1H-1-phenylmirazole-4-carboxaldehyde (1 eq), rhodanine (1.2 eq), and sodium acetate (1.2 eq) were added to an ethanol solution in a round bottom flask, followed by stirring at 60° C. for 15 hours. When the reaction was completed, the reaction suspension was cooled to room temperature, and the precipitate generated during the reaction was filtered, and then washed with a large amount of water, ethanol, and diethyl ether to obtain the desired compound in a yield of 89%.
1H NMR (300 MHz, DMSO-d6) δ 8.75 (s, 1H), 8.02 (s, 1H), 7.89 (d, 2H, J=8.1 Hz), 7.54 (t, 2H, J=7.8 Hz), 7.40-7.36 (m, 2H).

Exemplary Potassium Salt of Example 1-1. Preparation of Potassium Salt of (5Z)-5-[(1-phenylpyrazole-4-yl)methylene]-2-thioxo-thiazolidin-4-one The Example 1-1 compound (1 eq) and potassium hydroxide (1.1 eq) were added to a methanol solution, respectively, and stirred at 60° C. for 30 minutes to completely dissolve. The mixture was stirred at 60° C. for another 1 hour, and cooled to room temperature after completion of the reaction. The reaction product was obtained through filtration and washed with an appropriate amount of methanol to obtain a potassium salt of the compound of Example 1-1 (Example 1-1K).

Example 1-2. Preparation of (5Z)-3-(2-furylmethyl)-5-[(1-methylpyrazol-4-yl)methylene]-2-thioxo-thiazolidin-4-one 3-(furan-2-ylmethyl)-2-thioxothiazolidin-4-one synthesized from Reaction formula 1 and 1-methyl-1H-pyrazole-4-carbaldehyde were reacted in the same manner as in Example 1-1 to obtain the target compound.
1H NMR (500 MHz, DMSO-d6) δ 8.28 (s, 1H), 7.87 (s, 1H), 7.79 (s, 1H), 7.59 (d, 1H, J=1.0 Hz), 6.40 (s, 2H), 5.20 (s, 2H), 3.92 (s, 3H); ESI (m/z) 306 (MH+).

Example 1-3. Preparation of (5'Z)-3-methyl-5-[(1-phenylpyrazol-4-yl)methylene]-2-thioxo-thiazolidin-4-one The target compound was obtained by reacting 3-methyl-2-thioxothiazolidin-4-one and 1-phenyl-1H-pyrazole-4-carbaldehyde in the same manner as in Example 1-1.
1H NMR (400 MHz, CDCl3) δ 8.14 (s, 1H), 7.95 (s, 1H), 7.73 (d, 3H, J=8.0 Hz), 7.52 (t, 2H, J=7.8 Hz), 7.39 (t, 1H, J=7.4 Hz), 3.53 (s, 3H).

Example 1-4. Preparation of (5Z)-3-ethyl-5-[(1-phenylpyrazol-4-yl)methylene]-2-thioxo-thiazolidin-4-one The target compound was obtained by reacting 3-ethyl-2-thioxothiazolidin-4-one and 1-phenyl-1H-pyrazole-4-carbaldehyde in the same manner as in Example 1-1.
1H NMR (300 MHz, DMSO-d6) δ 8.91 (s, 1H), 8.18 (s, 1H), 7.94-7.91 (m, 2H), 7.80 (s, 1H), 7.58-7.56 (m, 2H), 7.44-7.39 (m, 1H), 4.07 (q, 2H, J=7.2 Hz), 1.20 (t, 3H, J=7.2 Hz).

Example 1-5. Preparation of (5Z)-3-allyl-5-[(1-phenylpyrazol-4-yl)methylene]-2-thioxo-thiazolidin-4-one The target compound was obtained by reacting 3-allyl-2-thioxothiazolidin-4-one and 1-phenyl-1H-pyrazole-4-carbaldehyde in the same manner as in Example 1-1.
1H NMR (400 MHz, CDCl3) δ 8.13 (s, 1H), 7.94 (s, 1H), 7.74-7.70 (m, 3H), 7.51 (t, 2H, J=7.8 Hz), 7.41-7.37 (m, 1H), 5.91-5.83 (m, 1H), 5.33-5.25 (m, 2H), 4.75 (d, 2H, J=5.6 Hz).

Example 1-6. Preparation of (5Z)-5-[[1-(2-fluorophenyl)pyrazol-4-yl]methylene]-2-thioxo-thiazolidin-4-one The target compound was obtained by reacting 2-thioxothiazolidin-4-one and 1-(2-fluorophenyl)-1H-pyrazole-4-carbaldehyde in the same manner as in Example 1-1.
1H NMR (400 MHz, DMSO-d6) δ 13.73 (s, 1H), 8.69-8.68 (m, 1H), 8.16 (s, 1H), 7.86-7.82 (m, 1H), 7.68 (s, 1H), 7.56-7.47 (m, 2H), 7.44-7.39 (m, 1H).

Example 1-7. Preparation of (5Z)-5-[[1-(3-fluorophenyl)pyrazol-4-yl]methylene]-2-thioxo-thiazolidin-4-one The target compound was obtained by reacting 2-thioxothiazolidin-4-one and 1-(3-fluorophenyl)-1H-pyrazole-4-carbaldehyde in the same manner as in Example 1-1.
1H NMR (400 MHz, DMSO-d6) δ 13.73 (s, 1H), 8.89 (s, 1H), 8.15 (s, 1H), 7.87-7.79 (m, 2H), 7.62-7.56 (m, 2H), 7.27-7.22 (m, 1H).

Example 1-8. Preparation of (5Z)-5-[[1-(4-fluorophenyl)pyrazol-4-yl]methylene]-2-thioxo-thiazolidin-4-one The target compound was obtained by reacting 2-thioxothiazolidin-4-one and 1-(4-fluorophenyl)-1H-pyrazole-4-carbaldehyde in the same manner as in Example 1-1.
1H NMR (400 MHz, DMSO-d6) δ 13.67 (s, 1H), 8.78 (s, 1H), 8.80 (s, 1H), 7.93-7.90 (m, 2H), 7.56 (s, 1H), 7.36 (t, 2H, J=8.8 Hz); ESI (m/z) 306 (MH+).

Example 1-9. Preparation of (5Z)-5-[[1-(2-chlorophenyl)pyrazol-4-yl]methylene]-2-thioxo-thiazolidin-4-one The target compound was obtained by reacting 2-thioxothiazolidin-4-one and 1-(2-chlorophenyl)-1H-pyrazole-4-carbaldehyde in the same manner as in Example 1-1.
1H NMR (300 MHz, DMSO-d6) δ 13.70 (s, 1H), 8.63 (s, 1H), 8.13 (s, 1H), 7.76-7.64 (m, 3H), 7.60-7.53 (m, 2H).

Example 1-10. Preparation of (5Z)-5-[[1-(2-chlorophenyl)pyrazol-4-yl]methylene]-3-methyl-2-thioxothiazolidin-4-one The target compound was obtained by reacting 3-methyl-2-thioxothiazolidin-4-one and 1-(2-chlorophenyl)-1H-pyrazole-4-carbaldehyde in the same manner as in Example 1-1.
1H NMR (400 MHz, CDCl3) δ 8.14 (s, 1H), 7.96 (s, 1H), 7.73 (s, 1H), 7.63-7.57 (m, 2H), 7.46-7.40 (m, 2H), 3.53 (s, 3H).

Example 1-11. Preparation of (5Z)-5-[[1-(2-chlorophenyl)pyrazol-4-yl]methylene]-3-ethyl-2-thioxothiazolidin-4-one The target compound was obtained by reacting 3-ethyl-2-thioxothiazolidin-4-one and 1-(2-chlorophenyl)-1H-pyrazole-4-carbaldehyde in the same manner as in Example 1-1.
1H NMR (300 MHz, DMSO-d6) δ 8.69 (s, 1H), 8.18 (s, 1H), 7.85 (s, 1H), 7.77-7.64 (m, 2H), 7.62-7.52 (m, 2H), 4.07 (q, 2H, J=7.2 Hz), 1.19 (t, 3H, J=7.2 Hz).

Example 1-12. Preparation of (5Z)-3-allyl-5-[[1-(2-chlorophenyl)pyrazol-4-yl]methylene]-2-thioxothiazolidin-4-one The target compound was obtained by reacting 3-allyl-2-thioxothiazolidin-4-one and 1-(2-chlorophenyl)-1H-pyrazole-4-carbaldehyde in the same manner as in Example 1-1.
1H NMR (300 MHz, DMSO-d6) δ 8.71 (s, 1H), 8.19 (s, 1H), 7.86 (s, 1H), 7.77-7.65 (m, 2H), 7.61-7.53 (m, 2H), 5.92-5.79 (m, 1H), 5.21-5.10 (m, 2H), 4.66-4.63 (m, 2H).

Example 1-13. Preparation of (5Z)-5-[[1-(3-chlorophenyl)pyrazol-4-yl]methylene]-2-thioxo-thiazolidin-4-one The target compound was obtained by reacting 2-thioxothiazolidin-4-one and 1-(3-chlorophenyl)-1H-pyrazole-4-carbaldehyde in the same manner as in Example 1-1.
1H NMR (300 MHz, DMSO-d6) δ 13.73 (s, 1H), 8.91 (s, 1H), 8.16 (s, 1H), 8.07-8.06 (m, 1H), 7.94-7.90 (m, 1H), 7.60-7.55 (m, 2H), 7.48-7.44 (m, 1H).

Example 1-14. Preparation of (5Z)-5-[[1-(3-chlorophenyl)pyrazol-4-yl]methylene]-3-methyl-2-thioxothiazolidin-4-one The target compound was obtained by reacting 3-methyl-2-thioxothiazolidin-4-one and 1-(3-chlorophenyl)-1H-pyrazole-4-carbaldehyde in the same manner as in Example 1-1.
1H NMR (400 MHz, CDCl3) δ 8.12 (s, 1H), 7.94 (s, 1H), 7.78 (s, 1H), 7.69 (s, 1H), 7.63-7.61 (m, 1H), 7.45 (t, 1H, J=8.2 Hz), 7.37-7.35 (m, 1H), 3.53 (s, 3H).

Example 1-15. Preparation of (5Z)-5-[[1-(3-chlorophenyl)pyrazol-4-yl]methylene]-3-ethyl-2-thioxothiazolidin-4-one The target compound was obtained by reacting 3-ethyl-2-thioxothiazolidin-4-one and 1-(3-chlorophenyl)-1H-pyrazole-4-carbaldehyde in the same manner as in Example 1-1.
1H NMR (300 MHz, DMSO-d6) δ 8.95 (s, 1H), 8.20 (s, 1H), 8.08-8.07 (m, 1H), 7.94-7.91 (m, 1H), 7.75 (s, 1H), 7.61-7.55 (m, 1H), 7.48-7.45 (m, 1H), 4.06 (q, 2H, J=7.2 Hz), 1.20 (., 3H, J=7.1 Hz).

Example 1-16. Preparation of (5Z)-3-allyl-5-[[1-(3-chlorophenyl)pyrazol-4-yl]methylene]-2-thioxothiazolidin-4-one The target compound was obtained by reacting 3-allyl 2-thioxothiazolidin-4-one with 1-(3-chlorophenyl)-1H-pyrazole-4-carbaldehyde in the same manner as in Example 1-1.
1H NMR (400 MHz, DMSO-d6) δ 8.96 (s, 1H), 8.22 (s, 1H), 8.08 (s, 1H), 7.94-7.92 (m, 1H), 7.77 (s, 1H), 7.58 (t, 1H, J=8.0 Hz), 7.48-7.46 (m, 1H), 5.90-5.81 (m, 1H), 5.21-5.12 (m, 2H), 4.65-4.64 (m, 2H).

Example 1-17. Preparation of (5Z)-5-[[1-(4-chlorophenyl)pyrazol-4-yl]methylene]-2-thioxo-thiazolidin-4-one The target compound was obtained by reacting 2-thioxothiazolidin-4-one and 1-(4-chlorophenyl)-1H-pyrazole-4-carbaldehyde in the same manner as in Example 1-1.
1H NMR (300 MHz, DMSO-d6) δ 13.72 (s, 1H), 8.87 (s, 1H), 7.96 (d, 2H, J=6.6 Hz), 7.62 (d, 2H, J=6.6 Hz), 7.59 (s, 1H).

Example 1-18. Preparation of (5Z)-5-[[1-(4-chlorophenyl)pyrazol-4-yl]methylene]-3-methyl-2-thioxothiazolidin-4-one The target compound was obtained by reacting 3-methyl-2-thioxothiazolidin-4-one and 1-(4-chlorophenyl)-1H-pyrazole-4-carbaldehyde in the same manner as in Example 1-1.
1H NMR (400 MHz, DMSO-d6) δ 8.92 (s, 1H), 8.20 (s, 1H), 7.97 (d, 2H, J=9.2 Hz), 7.78 (s, 1H), 7.63 (d, 2H, J=8.8 Hz), 3.40 (s, 3H).

Example 1-19. Preparation of (5Z)-5-[[1-(4-chlorophenyl)pyrazol-4-yl]methylene]-3-ethyl-2-thioxothiazolidin-4-one The target compound was obtained by reacting 3-ethyl-2-thioxothiazolidin-4-one and 1-(4-chlorophenyl)-1H-pyrazole-4-carbaldehyde in the same manner as in Example 1-1.
1H NMR (400 MHz, CDCl3) δ 8.09 (s, 1H), 7.93 (s, 1H), 7.68 (d, 3H, J=8.0 Hz), 7.48 (d, 2H, J=8.0 Hz), 4.19 (dd, 2H, J=14.2, 7.2 Hz), 1.30 (t, 3H, J=6.8 Hz).

Example 1-20. Preparation of (5Z)-5-[[1-(p-tolyl)pyrazol-4-yl]methylene]-2-thioxo-thiazolidin-4-one The target compound was obtained by reacting 2-thioxothiazolidin-4-one and 1-(4-methylphenyl)-1H-pyrazole-4-carbaldehyde in the same manner as in Example 1-1.
1H NMR (400 MHz, DMSO-d6) δ 13.71 (s, 1H), 8.80 (s, 1H), 8.09 (s, 1H), 7.80-7.78 (m, 2H), 7.60 (s, 1H), 7.36-7.34 (m, 2H), 2.36 (s, 3H).

Example 1-21. Preparation of (5Z)-3-methyl-5-[[1-(p-tolyl)pyrazol-4-yl]methylene]-2-thioxo-thiazolidin-4-one The target compound was obtained by reacting 3-methyl-2-thioxothiazolidin-4-one and 1-(4-methylphenyl)-1H-pyrazole-4-carbaldehyde in the same manner as in Example 1-1.
1H NMR (400 MHz, CDCl3) δ 8.09 (s, 1H), 7.92 (s, 1H), 7.71 (s, 1H), 7.61-7.58 (m, 2H), 7.31-7.29 (m, 2H), 3.53 (s, 3H), 2.42 (s, 3H).

Example 1-22. Preparation of (5Z)-3-ethyl-5-[[1-(p-tolyl)pyrazol-4-yl]methylene]-2-thioxo-thiazolidin-4-one The target compound was obtained by reacting 3-ethyl-2-thioxothiazolidin-4-one and 1-(4-methylphenyl)-1H-pyrazole-4-carbaldehyde in the same manner as in Example 1-1.

1H NMR (300 MHz, DMSO-d6) δ 8.85 (s, 1H), 8.15 (s, 1H), 7.82-7.81 (m, 3H), 7.37-7.34 (m, 2H), 4.07 (q, 2H, J=7.2 Hz), 2.37 (s, 3H), 1.29 (t, 3H, J=7.2 Hz).

Example 1-23. Preparation of (5Z)-3-allyl-5-[[1-(p-tolyl)pyrazol-4-yl]methylene]-2-thioxo-thiazolidin-4-one The target compound was obtained by reacting 3-allyl-2-thioxothiazolidin-4-one and 1-(4-methylphenyl)-1H-pyrazole-4-carbaldehyde in the same manner as in Example 1-1.

1H NMR (400 MHz, DMSO-d6) δ 8.85 (s, 1H), 8.15 (s, 1H), 7.81-7.79 (m, 3H), 7.36-7.34 (m, 2H), 5.90-5.81 (m, 1H), 5.21-5.11 (m, 2H), 4.65-4.63 (m, 2H), 2.36 (s, 3H).

Example 1-24. Preparation of (5Z)-5-[[1-(4-isopropylphenyl)pyrazol-4-yl]methylene]-2-thioxo-thiazolidin-4-one The target compound was obtained by reacting 2-thioxothiazolidin-4-one and 1-(4-isopropylphenyl)-1H-pyrazole-4-carbaldehyde in the same manner as in Example 1-1.

1H NMR (400 MHz, DMSO-d6) δ 13.71 (s, 1H), 8.81 (s, 1H), 8.10 (s, 1H), 7.82-7.80 (m, 2H), 7.61 (s, 1H), 7.43-7.40 (m, 2H), 3.01-2.91 (m, 1H), 1.24 (d, 6H, J=6.8 Hz).

Example 1-25. Preparation of (5Z)-3-ethyl-5-[[1-(4-isopropylphenyl)pyrazol-4-yl]methylene]-2-thioxo-thiazolidin-4-one The target compound was obtained by reacting 3-ethyl-2-thioxothiazolidin-4-one and 1-(4-isopropylphenyl)-1H-pyrazole-4-carbaldehyde in the same manner as in Example 1-1.

1H NMR (400 MHz, DMSO-d6) δ 8.86 (s, 1H), 8.15 (s, 1H), 7.82 (d, 2H, J=8.4 Hz), 7.78 (s, 1H), 7.42 (d, 2H, J=8.4 Hz), 4.06 (q, 2H, J=6.8 Hz), 2.93-3.00 (m, 1H), 1.24 (d, 6H, J=6.8 Hz), 1.19 (t, 3H, J=7.0 Hz).

Example 1-26. Preparation of (5Z)-5-[[1-(4-butylphenyl)pyrazol-4-yl]methylene]-2-thioxo-thiazolidin-4-one The target compound was obtained by reacting 2-thioxothiazolidin-4-one and 1-(4-butylphenyl)-1H-pyrazole-4-carbaldehyde in the same manner as in Example 1-1.

1H NMR (400 MHz, DMSO-d6) δ 13.71 (s, 1H), 8.81 (s, 1H), 8.10 (s, 1H), 7.81-7.79 (m, 2H), 7.61 (s, 1H), 7.37-7.35 (m, 2H), 2.63 (t, 2H, J=7.6 Hz), 1.62-1.54 (m, 2H), 1.37-1.27 (m, 2H), 0.91 (t, 3H, J=7.4 Hz).

Example 1-27. Preparation of (5Z)-5-[[1-(4-butylphenyl)pyrazol-4-yl]methylene]-3-ethyl-2-thioxo-thiazolidin-4-one The target compound was obtained by reacting 3-ethyl-2-thioxothiazolidin-4-one and 1-(4-butylphenyl)-1H-pyrazole-4-carbaldehyde in the same manner as in Example 1-1.

1H NMR (400 MHz, DMSO-d6) δ 8.85 (s, 1H), 8.15 (s, 1H), 7.78-7.82 (m, 3H), 7.36 (d, 2H, J=8.4 Hz), 4.06 (q, 2H, J=7.2 Hz), 2.64 (t, 2H, J=7.6 Hz), 1.55-1.62 (m, 2H), 1.28-1.37 (m, 2H), 1.19 (t, 3H, J=7.0 Hz), 0.91 (t, 3H, J=7.4 Hz).

Example 1-28. Preparation of (5Z)-5-[[1-(3,4-dimethylphenyl)pyrazol-4-yl]methylene]-2-thioxo-thiazolidin-4-one The target compound was obtained by reacting 2-thioxothiazolidin-4-one and 1-(3,4-dimethylphenyl)-1H-pyrazole-4-carbaldehyde in the same manner as in Example 1-1.

1H NMR (400 MHz, DMSO-d6) δ 13.70 (s, 1H), 8.76 (s, 1H), 8.07 (s, 1H), 7.71 (s, 1H), 7.61-7.58 (m, 2H), 7.30-7.28 (m, 1H), 2.31 (s, 3H), 2.26 (s, 3H).

Example 1-29. Preparation of (5Z)-5-[[1-(3,4-dimethylphenyl)pyrazol-4-yl]methylene]-3-ethyl-2-thioxo-thiazolidin-4-one Produce The target compound was obtained by reacting 3-ethyl-2-thioxothiazolidin-4-one and 1-(3,4-dimethylphenyl)-1H-pyrazole-4-carbaldehyde in the same manner as in Example 1-1.

1H NMR (400 MHz, DMSO-d6) δ 8.81 (s, 1H), 8.13 (s, 1H), 7.77 (s, 1H), 7.72 (s, 1H), 7.62-7.60 (m, 1H), 7.30-7.28 (m, 1H), 4.06 (q, 2H, J=7.2 Hz), 2.31 (s, 3H), 2.27 (s, 3H), 1.19 (t, 311, =7.0 Hz).

Example 1-30. Preparation of (5Z)-5-[[1-(2-methoxyphenyl)pyrazol-4-yl]methylene]-2-thioxo-thiazolidin-4-one The target compound was obtained by reacting 2-thioxothiazolidin-4-one and 1-(2-methoxyphenyl)-1H-pyrazole-4-carbaldehyde in the same manner as in Example 1-1.

1H NMR (400 MHz, DMSO-d6) δ 13.70 (s, 1H), 8.64 (s, 1H), 8.06 (s, 1H), 7.68-7.65 (m, 2H), 7.47-7.42 (m, 1H), 7.31-7.29 (m, 1H), 7.14-7.10 (m, 1H), 3.90 (s, 3H).

Example 1-31. Preparation of (5Z)-5-[[1-(2-naphthyl)pyrazol-4-yl]methylene]-2-thioxo-thiazolidin-4-one The target compound was obtained by reacting 2-thioxothiazolidin-4-one and 1-(naphthalen-2-yl)-1H-pyrazole-4-carbaldehyde in the same manner as in Example 1-1.

1H NMR (400 MHz, DMSO-d6) δ 13.73 (s, 1H), 8.98 (s, 1H), 8.48 (s, 1H), 8.19 (s, 1H), 8.11 (s, 1H), 8.06-7.99 (m, 2H), 7.64-7.55 (m, 3H).

Example 1-32. Preparation of (5Z)-3-ethyl-5-[[1-(2-naphthyl)pyrazol-4-yl]methylene]-2-thioxo-thiazolidin-4-one The target compound was obtained by reacting 3-ethyl-2-thioxothiazolidin-4-one and 1-(naphthalen-2-yl)-1H-pyrazole-4-carbaldehyde in the same manner as in Example 1-1.

1H NMR (300 MHz, DMSO-d6) δ 9.03 (s, 1H), 8.49 (s, 1H), 8.25 (s, 1H), 8.13-8.12 (m, 2H), 8.07-7.99 (m, 1H), 7.82 (s, 1H), 7.65-7.54 (m, 2H), 4.08 (q, 2H, J=7.2 Hz), 1.21 (t, 3H, J=7.1 Hz).

Example 1-33. Preparation of (5Z)-5-[[1-(2-pyridyl)pyrazol-4-yl]methylene]-2-thioxo-thiazolidin-4-one The target compound was obtained by reacting 2-thioxothiazolidin-4-one and 1-(pyridin-2-yl)-1H-pyrazole-4-carbaldehyde in the same manner as in Example 1-1.

1H NMR (400 MHz, DMSO-d6) δ 13.75 (s, 1H), 9.01 (s, 1H), 8.56-8.55 (m, 1H), 8.17 (s, 1H), 8.08-8.04 (m, 1H), 7.99-7.97 (m, 1H), 7.71 (s, 1H), 7.47-7.44 (m, 1H).

Example 1-34. Preparation of (5Z)-3-(2-hydroxyethyl)-5-[[1-(2-pyridyl)pyrazol-4-yl]methylene]-2-thioxo-thiazolidin-4-one 3-(2-hydroxyethyl)-2-thioxothiazolidin-4-one synthesized from Reaction formula 1 and 1-(pyridin-2-yl)-1H-pyrazole-4-carbaldehyde were reacted in the same manner as in Example 1-1 to obtain the target compound.
1H NMR (400 MHz, DMSO-d6) δ 9.07 (s, 1H), 8.56-8.55 (m, 1H), 8.23 (s, 1H), 8.09-8.05 (m, 1H), 8.00-7.98 (m, 1H), 4.94 (t, 1H, J=6.0 Hz), 4.12 (t, 2H, J=6.2 Hz), 3.66 (q, 2H, J=6.4 Hz).

Example 1-35. Preparation of (5Z)-5-[[1-(3-pyridyl)pyrazol-4-yl]methylene]-2-thioxo-thiazolidin-4-one The target compound was obtained by reacting 2-thioxothiazolidin-4-one and 1-(pyridin-3-yl)-1H-pyrazole-4-carbaldehyde in the same manner as in Example 1-1.
1H NMR (400 MHz, DMSO-d6) δ 13.74 (s, 1H), 8.17 (d, 1H, J=2.4 Hz), 8.94 (s, 1H), 8.62-8.60 (m, 1H), 8.35-8.31 (m, 1H), 8.21 (s, 1H), 7.62-7.59 (m, 2H).

Example 1-36. Preparation of (5Z)-3-(2-hydroxyethyl)-5-[[1-(3-pyridyl)pyrazol-4-yl]methylene]-2-thioxo-thiazolidin-4-one 3-(2-hydroxyethyl)-2-thioxothiazolidin-4-one synthesized from Reaction formula 1 and 1-(pyridin-3-yl)-1H-pyrazole-4-carbaldehyde were reacted in the same manner as in Example 1-1 to obtain the target compound.
1H NMR (400 MHz, DMSO-d6) δ 9.19 (d, 1H, J=2.4 Hz), 9.00 (s, 1H), 8.62-8.61 (m, 1H), 8.36-3.33 (m, 1H), 8.26 (s, 1H), 7.78 (s, 1H), 7.63-7.60 (m, 1H), 4.94 (t, 1H, J=6.0 Hz), 4.12 (t, 2H, J=6.2 Hz), 3.66 (q, 2H, J=6.0 Hz).

Example 1-37. Preparation of (5Z)-5-[(5-methyl-1-phenyl-pyrazol-4-yl)methylene]-2-thioxo-thiazolidin-4-one The target compound was obtained by reacting 2-thioxothiazolidin-4-one and 5-methyl-1-phenyl-1H-pyrazole-4-carbaldehyde in the same manner as in Example 1-1.
1H NMR (300 MHz, DMSO-d6) δ 13.70 (s, 1H), 8.54 (s, 1H), 7.97-7.94 (m, 2H), 7.54-7.49 (m, 2H), 7.41-7.34 (m, 2H), 2.42 (s, 3H).

Example 1-38. Preparation of (5Z)-5-[(3,5-dimethyl-1-phenyl-pyrazol-4-yl)methylene]-2-thioxothiazolidin-4-one The target compound was obtained by reacting 2-thioxothiazolidin-4-one and 3,5-dimethyl-1-phenyl-1H-pyrazole-4-carbaldehyde in the same manner as in Example 1-1.
1H NMR (300 MHz, DMSO-d6) δ 13.68 (s, 1H), 7.56-7.43 (m, 6H), 2.34 (s, 3H), 2.31 (s, 3H).

Example 1-39. Preparation of (5Z)-5-[(1-phenylpyrazol-4-yl)methylene]thiazolidine-2,4-dione The target compound was obtained by reacting Thiazolidine-2,4-dione and 1-phenyl-1H-pyrazole-4-carbaldehyde in the same manner as in Example 1-1.
1H NMR (300 MHz, DMSO-d6) δ 12.48 (s, 1H), 8.83 (s, 1H), 7.91-7.87 (m, 2H), 7.74 (s, 1H), 7.58-7.53 (m, 2H), 7.42-7.37 (m, 1H).

Example 1-40. Preparation of (5Z)-5-[[1-(2-fluorophenyl)pyrazol-4-yl]methylene]thiazolidine-2,4-dione The target compound was obtained by reacting Thiazolidine-2,4-dione and 1-(2-fluorophenyl)-1H-pyrazole-4-carbaldehyde in the same manner as in Example 1-1.
1H NMR (400 MHz, DMSO-d6) δ 12.50 (s, 1H), 8.64-8.63 (m, 1H), 8.13 (s, 1H), 7.86-7.81 (m, 2H), 7.56-7.48 (m, 2H), 7.44-7.38 (m, 1H); ESI m/z 288[M-H].

Example 1-41. Preparation of (5Z)-5-[[1-(3-fluorophenyl)pyrazol-4-yl]methylene]thiazolidine-2,4-dione The target compound was obtained by reacting Thiazolidine-2,4-dione and 1-(3-fluorophenyl)-1H-pyrazole-4-carbaldehyde in the same manner as in Example 1-1.
1H NMR (400 MHz, DMSO-d6) δ 12.51 (s, 1H), 8.85 (s, 1H), 8.11 (s, 1H), 7.83-7.76 (m, 2H), 7.71 (s, 1H), 7.62-7.56 (m, 1H), 7.26-7.21 (m, 1H); ESI m/z 288[M-H].

Example 1-42. Preparation of (5Z)-5-[[1-(4-fluorophenyl)pyrazol-4-yl]methylene]thiazolidine-2,4-dione The target compound was obtained by reacting Thiazolidine-2,4-dione and 1-(4-fluorophenyl)-1H-pyrazole-4-carbaldehyde in the same manner as in Example 1-1.
1H NMR (300 MHz, DMSO-d6) δ 8.67 (s, 1H), 8.00 (s, 1H), 7.96-7.87 (m, 2H), 7.45-7.35 (m, 3H).

Example 1-43. Preparation of (5Z)-5-[[1-(2-chlorophenyl)pyrazol-4-yl]methylene]thiazolidine-2,4-dione The target compound was obtained by reacting Thiazolidine-2,4-dione and 1-(2-chlorophenyl)-1H-pyrazole-4-carbaldehyde in the same manner as in Example 1-1.
1H NMR (400 MHz, DMSO-d6) δ 8.42 (s, 1H), 8.01 (s, 1H), 7.74-7.65 (m, 2H), 7.55-7.50 (m, 3H).

Example 1-44. Preparation of (5Z)-5-[[1-(3-chlorophenyl)pyrazol-4-yl]methylene]thiazolidine-2,4-dione The target compound was obtained by reacting Thiazolidine-2,4-dione and 1-(3-chlorophenyl)-1H-pyrazole-4-carbaldehyde in the same manner as in Example 1-1.
1H NMR (400 MHz, DMSO-d6) δ 8.76 (s, 1H), 8.03-8.01 (m, 2H), 7.89-7.87 (m, 1H), 7.58-7.54 (m, 1H), 7.43-7.42 (m, 2H).

Example 1-45. Preparation of (5Z)-5-[[1-(4-chlorophenyl)pyrazol-4-yl]methylene]thiazolidine-2,4-dione The target compound was obtained by reacting Thiazolidine-2,4-dione and 1-(4-chlorophenyl)-1H-pyrazole-4-carbaldehyde in the same manner as in Example 1-1.
1H NMR (300 MHz, DMSO-d6) δ 8.71 (s, 1Ii), 8.02 (s, 1H), 7.93-7.90 (d, 2H), 7.62-7.59 (m, 2H), 7.45 (s, 1H).

Example 1-46. Preparation of (5Z)-5-[[1-(p-tolyl)pyrazol-4-yl]methylene]thiazolidine-2,4-dione The target compound was obtained by reacting Thiazolidine-2,4-dione and 1-(4-methylphenyl)-1H-pyrazole-4-carbaldehyde in the same manner as in Example 1-1.

1H NMR (400 MHz, DMSO-d6) δ 12.48 (s, 1H), 8.77 (s, 1H), 8.06 (s, 1H), 7.78-7.73 (m, 3H), 7.36-7.34 (m, 2H), 2.36 (s, 3H).

Example 1-47. Preparation of (5Z)-5-[[1-(4-isopropylphenyl)pyrazol-4-yl]methylene]thiazolidine-2,4-dione The target compound was obtained by reacting Thiazolidine-2,4-dione and 1-(4-isopropylphenyl)-1H-pyrazole-4-carbaldehyde in the same manner as in Example 1-1.

1H NMR (400 MHz, DMSO-d6) δ 12.47 (s, 1H), 8.77 (s, 1H), 8.06 (s, 1H), 7.80-7.73 (m, 3H), 7.42-7.40 (m, 2H), 3.01-2.91 (m, 1H), 1.23 (d, 61H, J=6.8 Hz).

Example 1-48. Preparation of (5Z)-5-[[1-(4-butylphenyl)pyrazol-4-yl]methylene]thiazolidine-2,4-dione The target compound was obtained by reacting Thiazolidine-2,4-dione and 1-(4-butylphenyl)-1H-pyrazole-4-carbaldehyde in the same manner as in Example 1-1.

1H NMR (300 MHz, DMSO-d6) δ 8.63 (s, 1H), 7.97 (s, 1H), 7.76 (d, 2H, J=8.7 Hz), 7.45 (s, 1H), 7.45 (d, 2H, J=8.4 Hz), 2.63 (t, 2H, J=7.5 Hz), 1.53-1.64 (m, 2H), 1.26-1.39 (m, 2H), 0.91 (t, 3H, J=7.4 Hz).

Example 1-49. Preparation of (5Z)-5-[[1-(3,4-dimethylphenyl)pyrazol-4-yl]methylene]thiazolidine-2,4-dione The target compound was obtained by reacting Thiazolidine-2,4-dione and 1-(3,4-dimethylphenyl)-1H-pyrazole-4-carbaldehyde in the same manner as in Example 1-1.

1H NMR (400 MHz, DMSO-d6) δ 12.48 (s, 1H), 8.74 (s, 1H), 8.04 (s, 1H), 7.72-7.69 (m, 214), 7.60-7.57 (m, 1H), 7.30-7.28 (m, 1H), 2.31 (s, 3H), 2.26 (s, 3H).

Example 1-50. Preparation of (5Z)-5-[[1-(2-methoxyphenyl)pyrazol-4-yl]methylene]thiazolidine-2,4-dione The target compound was obtained by reacting Thiazolidine-2,4-dione and 1-(2-methoxyphenyl)-1H-pyrazole-4-carbaldehyde in the same manner as in Example 1-1.

1H NMR (400 MHz, DMSO-d6) δ 12.46 (s, 1H), 8.59 (s, 1H), 8.03 (s, 1H), 7.80 (s, 1H), 7.68-7.65 (m, 1H), 7.46-7.42 (m, 1H), 7.30-7.28 (m, 1H), 7.14-7.10 (m, 1H), 3.90 (s, 3H).

Example 1-51. Preparation of (5Z)-5-[[1-(2-naphthyl)pyrazol-4-yl]methylene]thiazolidine-2,4-dione The target compound was obtained by reacting Thiazolidine-2,4-dione and 1-(naphthalen-2-yl)-1H-pyrazole-4-carbaldehyde in the same manner as in Example 1-1.

1H NMR (300 MHz, DMSO-d6) δ 8.83 (s, 1H), 8.42 (s, 1H), 7.98-8.10 (m, 5H), 7.53-7.63 (m, 2H), 7.50 (s, 1H).

Example 1-52. Preparation of (5Z)-5-[[1-(3-pyridyl)pyrazol-4-yl]methylene]thiazolidine-2,4-dione The target compound was obtained by reacting Thiazolidine-2,4-dione and 1-(pyridin-3-yl)-1H-pyrazole-4-carbaldehyde in the same manner as in Example 1-1.

1H NMR (400 MHz, DMSO-d6) δ 12.51 (s, 1H), 9.16-9.15 (m, 1H), 8.91 (s, 1H), 8.61-8.59 (m, 1H), 8.32-8.29 (m, 1H), 8.17 (s, 1H), 7.72 (s, 1H), 7.62-7.59 (m, 1H).

Example 1-53. Preparation of (5Z)-5-[(3-methyl-1-phenyl-pyrazol-4-yl)methylene]thiazolidine-2,4-dione The target compound was obtained by reacting Thiazolidine-2,4-dione and 3-methyl-1-phenyl-1H-pyrazole-4-carbaldehyde in the same manner as in Example 1-1.

1H NMR (300 MHz, DMSO-d6) δ 12.49 (s, 1H), 8.49 (s, 1H), 7.92 (d, 2H, J=7.5 Hz), 7.50-7.56 (m, 3H), 7.34-7.39 (m, 1H), 2.41 (s, 3H).

Example 1-54. Preparation of (5Z)-5-[(3,5-dimethyl-1-phenyl-pyrazol-4-yl)methylene]thiazolidine-2,4-dione The target compound was obtained by reacting Thiazolidine-2,4-dione and 3,5-dimethyl-1-phenyl-1H-pyrazole-4-carbaldehyde in the same manner as in Example 1-1.

1H NMR (400 MHz, CDCl3) δ 8.57 (s, 1H), 7.81 (s, 1H), 7.52-7.49 (m, 214), 7.44-7.43 (m, 3H), 2.38 (s, 3H), 2.34 (s, 3H); 13C NMR (100 MHz, DMSO-d6) δ 168.3, 167.4, 148.0, 139.5, 139.0, 129.6 (2), 128.4, 125.4, 125.0 (2), 124.1, 114.5, 13.5, 12.9.

Example 1-55. Preparation of (5Z)-5-[[1-(4-chlorophenyl)pyrazol-3-yl]methylene]-2-thioxo-thiazolidin-4-one 1-(4-chlorophenyl)-1H-pyrazole-3-carbaldehyde synthesized from Reaction formula 2 and 2-thioxothiazolidin-4-one were reacted in the same manner as in Example 1-1 to obtain the target compound.

1H NMR (400 MHz, DMSO-d6) δ 13.72 (s, 1H), 8.73 (d, 1H, J=2.4 Hz), 7.96 (d, 2H, J=8.8 Hz), 7.67 (d, 2H, J=8.8H), 7.58 (s, 1H), 7/02 (d, 1H, J=2.4 Hz).

Example 1-56. Preparation of (5Z)-5-[[1-(2-pyridyl)pyrazol-3-yl]methylene]-2-thioxo-thiazolidin-4-one 1-(pyridin-2-yl)-1H-pyrazole-3-carbaldehyde synthesized from Reaction formula 2 and 2-thioxothiazolidin-4-one were reacted in the same manner as in Example 1-1 to obtain the target compound.

1H NMR (400 MHz, DMSO-d6) δ 13.73 (s, 1H), 8.76 (s, 1H), 8.54-8.54 (m, 1H), 8.16-8.12 (m, 1H), 8.01-7.98 (m, 1H), 7.62 (s, 1H), 7.46 (t, 1H, J=5.6 Hz), 7.03 (s, 1H).

Example 1-57. Preparation of (5Z)-5-[[1-(3-pyridyl)pyrazol-3-yl]methylene]-2-thioxo-thiazolidin-4-one 1-(pyridin-3-yl)-1H-pyrazole-3-carbaldehyde synthesized from Reaction formula 2 and 2-thioxothiazolidin-4-one were reacted in the same manner as in Example 1-1 to obtain the target compound.

1H NMR (400 MHz, DMSO-d6) δ 13.66 (s, 1H), 9.14 (s, 1H), 8.73 (s, 1H), 8.55-8.54 (m, 1H), 8.27 (d, 1H, J=8.4 Hz), 7.61-7.57 (m, 1H), 7.53 (s, 1H), 6.70 (s, 1H).

Example 1-58. Preparation of (5Z)-5-[[1-phenylpyrazol-3-yl]methylene]thiazolidine-2,4-dione 1-phenyl-1H-pyrazole-3-carbaldehyde synthesized from Reaction formula 2 and Thiazolidine-2,4-dione were reacted in the same manner as in Example 1-1 to obtain the target compound.

1H NMR (400 MHz, DMSO-d6) δ 12.5 (s, 1H), 8.69 (s, 1H), 7.94 (d, 2H, J=8.0 Hz), 7.73 (s, 1H), 7.58 (t, 2H, J=8.0 Hz), 7.39 (t, 1H, J=7.4 Hz), 6.97 (s, 1H).

Example 1-59. Preparation of (5Z)-5-[[1-(2-pyridyl) pyrazol-3-yl]methylene]thiazolidine-2,4-dione 1-(pyridin-2-yl)-1H-pyrazole-3-carbaldehyde synthesized from Reaction formula 2 and Thiazolidine-2,4-dione were reacted in the same manner as in Example 1-1 to obtain the target compound.

1H NMR (400 MHz, DMSO-d6) δ 12.49 (s, 1H), 8.75 (s, 1H), 8.53-8.53 (m, 1H), 8.12-8.09 (m, 1H), 7.99-7.97 (m, 1H), 7.75 (s, 1H), 7.45 (t, 1H, J=5.6 Hz), 6.99 (s, 1H).

Examples 1-60. Preparation of (5Z)-5-[[1-(3-pyridyl)pyrazol-3-yl]methylene]thiazolidine-2,4-dione 1-(pyridin-3-yl)-1H-pyrazole-3-carbaldehyde synthesized from Reaction formula 2 and Thiazolidine-2,4-dione were reacted in the same manner as in Example 1-1 to obtain the target compound.

1H NMR (400 MHz, DMSO-d6) δ12.49 (s, 1H), 9.20 (s, 1H), 8.78 (s, 1H), 8.60-8.59 (m, 1H), 8.32 (d, 1H, J=8.4 Hz), 7.73 (s, 1H), 7.65-7.62 (m, 1H), 7.02 (s, 1H).

Example 1-61. Preparation of (5Z)-5-[[1-(4-pyridyl)pyrazol-3-yl]methylene]thiazolidine-2,4-dion Thiazolidine-2,4-dione and 1-(pyridin-4-yl)-1H-pyrazole-3-carbaldehyde synthesized from Reaction Formula 2 were reacted in the same manner as in the Example 1-1 to obtain the target compound.

1H NMR (400 MHz, DMSO-d6) δ 12.51 (s, 1H), 8.86 (s, 1H), 8.73-8.72 (m, 2H), 7.94-7.93 (m, 2H), 7.71 (s, 1H), 7.03 (s, 1H).

Example 2: Evaluation of mTORC1 Activity Inhibitory Effect 2-1. Evaluation of mTORC1 Activity Inhibitory Effect (1)

In order to evaluate the inhibitory effect of the compounds according to the present invention on the activity of mTORC1, an experiment was performed in the following manner.

The colorectal cancer cell line SW620 was purchased from the American Type Culture Collection (ATCC). The cell line was dispensed into a 24-well plate, cultured for 24 hours, treated for 1 hour 30 minutes in a medium containing no leucine amino acid, and then cultured again for 15 minutes in a medium containing leucine. The compounds of the Examples 1-1 to 1-62 were added when cultured in a medium containing leucine at a final concentration of 20 µM. 20 µg of cell lysate was separated by electrophoresis, and analyzed by Western blot method using phospho-p70 S6 Kinase (Thr380) antibody (#9206, Cell Signaling Technology) to see mTORC1 activity. The effect of inhibiting mTORC1 activity was evaluated by comparing the negative control group treated with only DMSO and the group treated with the compound in each well.

TABLE 2

| Example | mTORC1 inhibitory effect (%, 20 µM) inhibitory effect (%) |
|---|---|
| 1-1 | 98.54 ± 0.33 |
| 1-2 | 74.4 ± 0.2 |
| 1-3 | 53.97 ± 1.49 |
| 1-4 | 68.36 ± 1.69 |
| 1-5 | 45.82 ± 3.59 |
| 1-6 | 86.58 ± 2.50 |
| 1-7 | 88.23 ± 0.55 |
| 1-8 | 97.1 ± 1.8 |
| 1-9 | 92.76 ± 1.09 |
| 1-10 | 50.52 ± 3.69 |
| 1-11 | 67.22 ± 1.41 |
| 1-12 | 70.93 ± 2.39 |
| 1-13 | 94.90 ± 0.77 |
| 1-14 | 46.72 ± 14.22 |
| 1-15 | 72.46 ± 1.79 |
| 1-16 | 3.74 ± 10.43 |
| 1-17 | 86.7 ± 3.1 |
| 1-18 | 50.17 ± 12.77 |
| 1-19 | 54.17 ± 8.55 |
| 1-20 | 83.30 ± 1.76 |
| 1-21 | 71.18 ± 5.04 |
| 1-22 | 77.21 ± 0.84 |
| 1-23 | 15.74 ± 10.22 |
| 1-24 | 93.18 ± 2.50 |
| 1-25 | 36.86 ± 3.47 |
| 1-26 | 59.73 ± 3.55 |
| 1-27 | 51.70 ± 7.12 |
| 1-28 | 47.13 ± 3.15 |
| 1-29 | 4.02 ± 6.64 |
| 1-30 | 88.27 ± 1.18 |
| 1-31 | 40.20 ± 1.02 |
| 1-32 | 75.04 ± 5.32 |
| 1-33 | 93.50 ± 1.59 |
| 1-34 | 82.94 ± 1.10 |
| 1-35 | 96.45 ± 0.55 |
| 1-36 | 80.88 ± 1.10 |
| 1-37 | 96.82 ± 0.71 |
| 1-38 | 75.78 ± 2.60 |
| 1-39 | 93.53 ± 1.84 |
| 1-40 | 41.03 ± 0.21 |
| 1-41 | 49.37 ± 7.34 |
| 1-42 | 73.81 ± 2.77 |
| 1-43 | 52.34 ± 3.97 |
| 1-44 | 50.76 ± 5.28 |
| 1-45 | 64.18 ± 3.13 |
| 1-46 | 74.39 ± 0.62 |
| 1-47 | 74.36 ± 1.23 |
| 1-48 | 69.53 ± 2.04 |
| 1-49 | 68.36 ± 2.99 |
| 1-50 | 38.93 ± 16.04 |
| 1-51 | 53.08 ± 1.81 |
| 1-52 | 93.50 ± 1.38 |
| 1-53 | 71.70 ± 1.70 |
| 1-54 | 71.17 ± 4.46 |
| 1-55 | 74.6 ± 6.5 |
| 1-56 | 97.04 ± 0.65 |
| 1-57 | 90.20 ± 1.29 |
| 1-58 | 59.51 ± 4.35 |
| 1-59 | 91.00 ± 1.78 |
| 1-60 | 81.52 ± 3.79 |
| 1-61 | 91.50 ± 1.30 |
| 1-62 | 98.26 ± 0.16 |

As shown in the Table 2, it can be seen that the compounds according to the present invention significantly inhibit the activity of mTORC1 at 20 uM. In particular, it was confirmed that the compounds of Example 1-1, Example 1-1K (potassium salt of Example 1-1) Example 1-6, Example 1-7, Example 1-8, Example 1-9, Example 1-13, Example 1-17, Example 1-24, Example 1-30, Example 1-33, Example 1-35, Example 1-37, Example 1-39, Example 1-52, Examples 1-56, 1-57, Examples 1-59, and 1-61 exhibit an excellent inhibitory effect of 85% or more at a concentration of 20 uM.

Therefore, the compound of Chemical Formula 1 according to the present invention has excellent activity to inhibit mTOR, which is closely related to the process of epileptogenesis and autodigestion, thus it could be determined that it could show the effect of preventing or treating brain diseases related to the mTOR pathway.

2-2. Evaluation of mTORC1 Activity Inhibitory Effect (IC50) (2)

In order to evaluate the activity inhibitory effect (IC50) of the compounds selected in the Example 2-1 on mTORC1, an experiment was performed in the following manner.

The colorectal cancer cell line SW620 was purchased from the American Type Culture Collection (ATCC). The cell line was dispensed into a 24-well plate and cultured for 24 hours, and then each of the selected compounds (final concentration 0.1, 0.5, 1, 2, 5, 10, 20 μM) was added during culture for 6 hours in a medium containing 10% FBS. 20 μg of cell lysate was separated by electrophoresis, and analyzed by Western blot method using phospho-p70 S6 Kinase (Thr380) antibody (#9206, Cell Signaling Technology) to see mTORC1 activity. The effect of inhibiting mTORC1 activity was evaluated by comparing the negative control group treated with only DMSO and the group treated with the compound in each well.

TABLE 3

| Evaluation of mTORC1 inhibitory effect (IC50 μM) | |
|---|---|
| Example | inhibitory effect IC50 (μM) |
| 1-1 | 0.045 ± 0.002 |
| 1-6 | 0.1237 ± 0.0235 |
| 1-7 | 0.0917 ± 0.0012 |
| 1-8 | 0.086 ± 0.002 |
| 1-9 | 0.1623 ± 0.0279 |
| 1-13 | 0A298 ± 0.0073 |
| 1-17 | 0.069 ± 0.004 |
| 1-24 | 0.0890 ± 0.0094 |
| 1-30 | 0.0942 ± 0.0019 |
| 1-33 | 0.0896 ± 0.0289 |
| 1-35 | 0.0872 ± 0.0146 |
| 1-37 | 0.0799 ± 0.0113 |
| 1-39 | 0.1076 ± 0.0133 |
| 1-52 | 0.0934 ± 0.0197 |
| 1-56 | 0.083 ± 0.010 |
| 1-57 | 0.103 ± 0.015 |
| 1-59 | 0.216 ± 0.038 |
| 1-61 | 0.094 ± 0.019 |
| 1-1K | 0.024 ± 0.004 |

Among the compounds of the Examples 1-1 to 1-61, compounds that showed excellent inhibitory activity (inhibitory activity of 85% or more at 20 μM) were selected to further evaluate the inhibitory activity of mTORC1.

As a result, as shown in the Table 3, it was confirmed that each compound had an IC50 of 1 μM or less, and furthermore, it was confirmed that some compounds exhibited very excellent effects of an IC50 of 100 nM or less.

2-3. Confirmation of Changes in Phosphorylation of S6K Protein in Cells Expressing Mutant mTOR S6K, a sub-regulator of the mTOR pathway, is directly related to mTOR activity. That is, since activated mTOR phosphorylates the T389 residue of S6K, the activity of mTOR can be confirmed by evaluating the degree of phosphorylation of S6K.

Accordingly, the present inventors treated the compound of the Example 1-1 and a salt thereof, which were found to exhibit the best mTOR inhibitory activity in Example 2-1, to NIH3T3 cells carrying the mTOR mutation (C1483Y) known to cause epilepsy. After that, an experiment was conducted to confirm the degree of phosphorylation of S6K. As a positive control, the compound of Example 1-214 described in Korean Patent Application Laid-Open No. 10-2017-0107404 (indicated as "0186" in the Figures) was used.

Specifically, NIH3T3 cells carrying the C1483Y mutation were treated with 20 μM of the Example 1-1 compound or a salt thereof for 6 hours, deficient in leucine for 90 minutes, and then restimulated with leucine for 15 minutes. Cell lysates were immunoblotted with anti-phospho S6K antibody (Cell Signaling Technology, #9205) to analyze the degree of phosphorylation of S6K. The results are shown in FIGS. 1a and 1b.

Figure 1B:
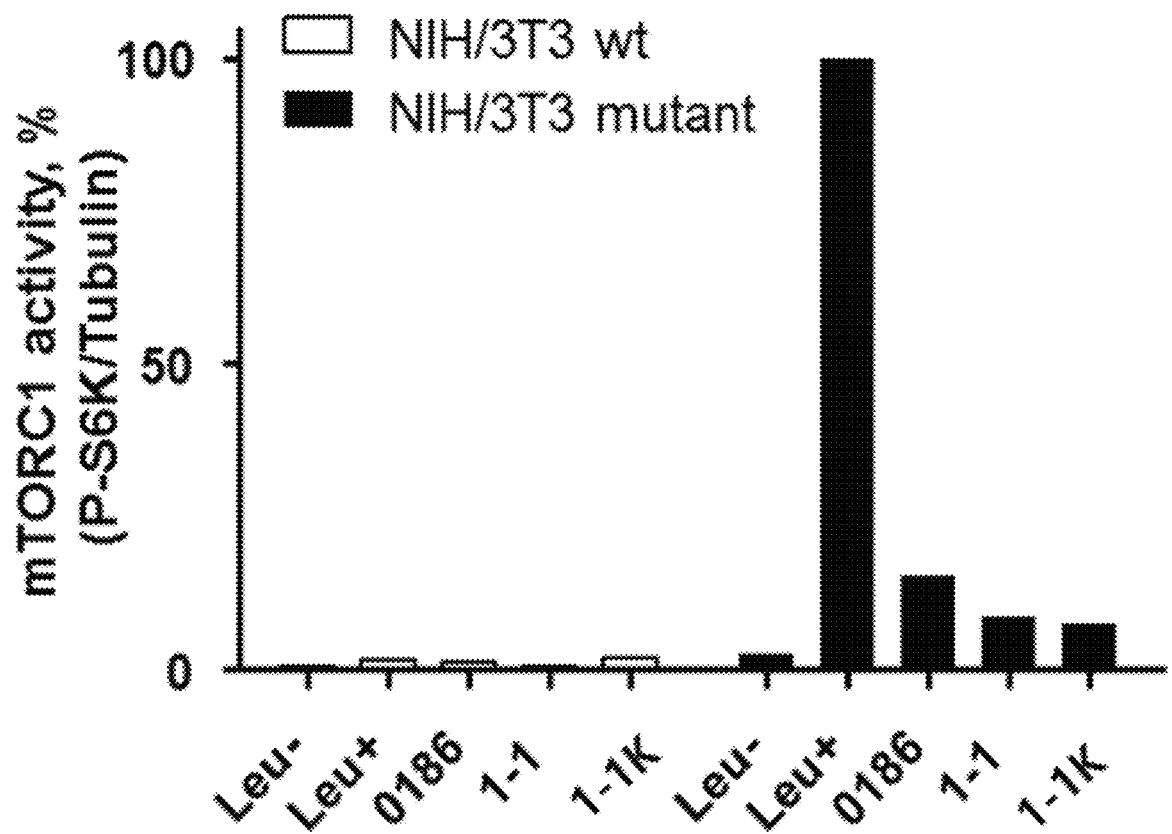

As shown in FIGS. 1a and 1b, it was confirmed that when leucine was treated with NIH3T3 cells carrying the mTOR C1483Y mutation, phosphorylation of S6K was significantly increased compared to wild-type NIH3T3 cells. On the other hand, as a result of treatment with the compound of Example 1-1 or a salt thereof to the cells treated with leucine, it was confirmed that phosphorylation of S6K was significantly reduced, through this, it was confirmed once again that the compound according to the present invention is a strong inhibitor of mTOR activity.

Example 3: Evaluation of Binding Inhibitory Activity of LRS and RagD

After confirming that the compounds of Chemical Formula 1 in Example 2 are very excellent in inhibiting the activity of mTOR, the present inventor attempted to confirm the mechanism by which these compounds inhibit the activity of mTOR.

As described above, leucyl tRNA synthetase (LRS) functions as a key mediator for amino acid signaling to mTORC1. LRS directly binds to Rag GTPase, which is an amino acid-dependent signaling mediator to mTORC1, and acts as a GTPase-activating protein (GAP) for Rag GTPase, so that Rag GTPase activates mTORC1.

Therefore, when the binding of LRS and RagD is blocked, the decomposition of GTP of RagD is reduced, and as a result, the activity of mTOR is suppressed.

3-1. RagD GTP Hydrolysis Inhibitory Activity (GTP-Agarose Bead Pulldown Assay)

GTP-agarose bead pulldown assay was performed to analyze RagD bound to GTP.

SW620 cells were treated with 10 μM of the Example 1-4 compound or a salt thereof for 1 hour, deficient in leucine for 90 minutes, and then restimulated with leucine for 15 minutes. After washing the cells with cold PBS, cells were obtained in GTP-binding buffer (20 mM Tris-HCl, pH 7.5, 5 mM MgCl$_2$, 2 mM PMSF, 20 μg/ml leupeptin, 10 μg/ml aprotinin, 150 mM NaCl, 1% Triton X-100, 1× phosphatase inhibitor cocktail). The cells were sonicated for 15 seconds to lyse, and the cell lysate was centrifuged at 4° C. for 10 minutes and at 13000×g to obtain a supernatant. The obtained protein solution (contained in 500 μl of GTP-binding buffer) was treated with 100 μl of GPT-agarose bead (Sigma Aldrich, Cat no. G9768) and left at 4° C. for 30 minutes. Thereafter, the beads were washed with GTP-binding buffer, and the supernatant was recovered. The washed beads in the recovered supernatant were once again treated for 30 minutes. The beads were washed again, and the recovered supernatant was left overnight at 4° C. After washing 5 times with GTP-binding buffer to separate contaminants that may have been included, the GTP-binding protein was analyzed by performing immunoblot analysis using anti-RagD or ARF1 antibody. ARF1 was used as a negative control. As a positive control, the compound of Example 1-214 described in Korean Patent Application Laid-Open No. 10-2017-0107404 (indicated as "0186" in the Figures) was used.

Figure 2:
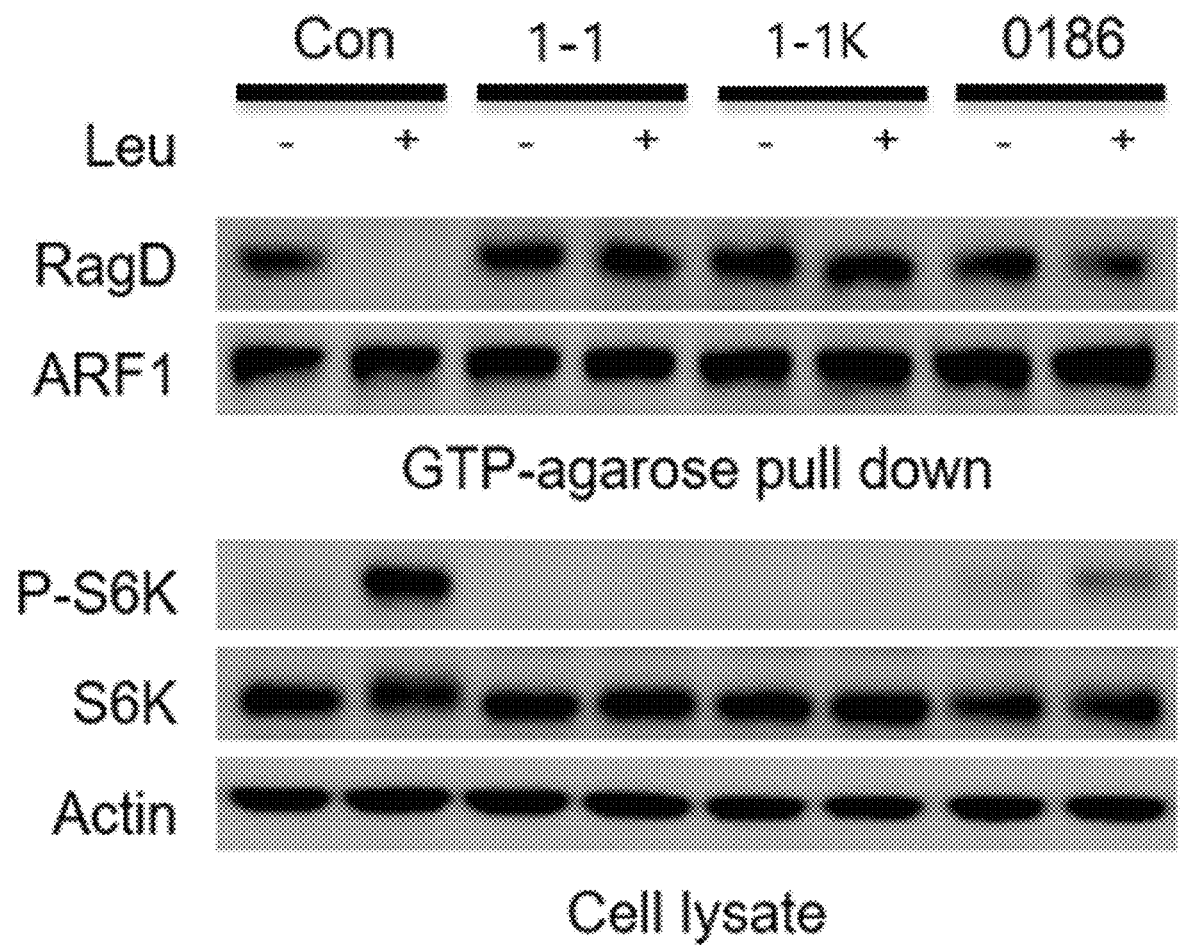
FIG. 2 is a immunoblot result of GTP hydrolysis of RagD after treating the compound of Example 1-1 or a salt thereof on SW620 cells (Leu: leucine)

The results are shown in FIG. 2.

As shown in FIG. 2, in the control group (Con) not treated with the compound, RagD was not detected when leucine was treated. In other words, it was confirmed that GTP was hydrolyzed in RagD by LRS and thus no detection was made. In contrast, in the test group treated with the compound of the Example 1-1 or a salt thereof, RagD was detected to a similar degree to that of the control group not treated with leucine, this means that the compound of Example 1-1 or a salt thereof inhibited the activity of LRS, thereby inhibiting the GTP hydrolysis of RagD by leucine treatment.

3-2. Direct Inhibitory Activity on the Interaction of LRS and RagD

In Example 3-1, it was confirmed that the compound according to the present invention or a salt thereof has an activity of inhibiting GTP hydrolysis of RagD by LRS.

Accordingly, the present inventors then tried to determine whether the compound according to the present invention directly inhibits the interaction between LRS and RagD.

SW620 cells were treated with 10 uM of the Example 1-1 compound or a salt thereof for 1 hour, deficient in leucine for 90 minutes, and then restimulated with leucine for 15 minutes. Cells were lysed using a lysis buffer containing a protease inhibitor, and a primary antibody was added to the cell lysate for immunoprecipitation, followed by stirring at 4° C. for 2 hours and allowed to stand. A 50% protein agarose G-Sepharose slurry was added and left for an additional 4 hours. After washing three times with cold lysis buffer, the precipitate was dissolved in SDS sample buffer, separated by SDS-PAGE, and immunoblotted using anti-LRS or anti-RagD antibody. As a positive control, the compound of Example 1-214 described in Korean Patent Application Laid-Open No. 10-2017-0107404 (indicated as "0186" in the Figures) was used.

Figure 3:
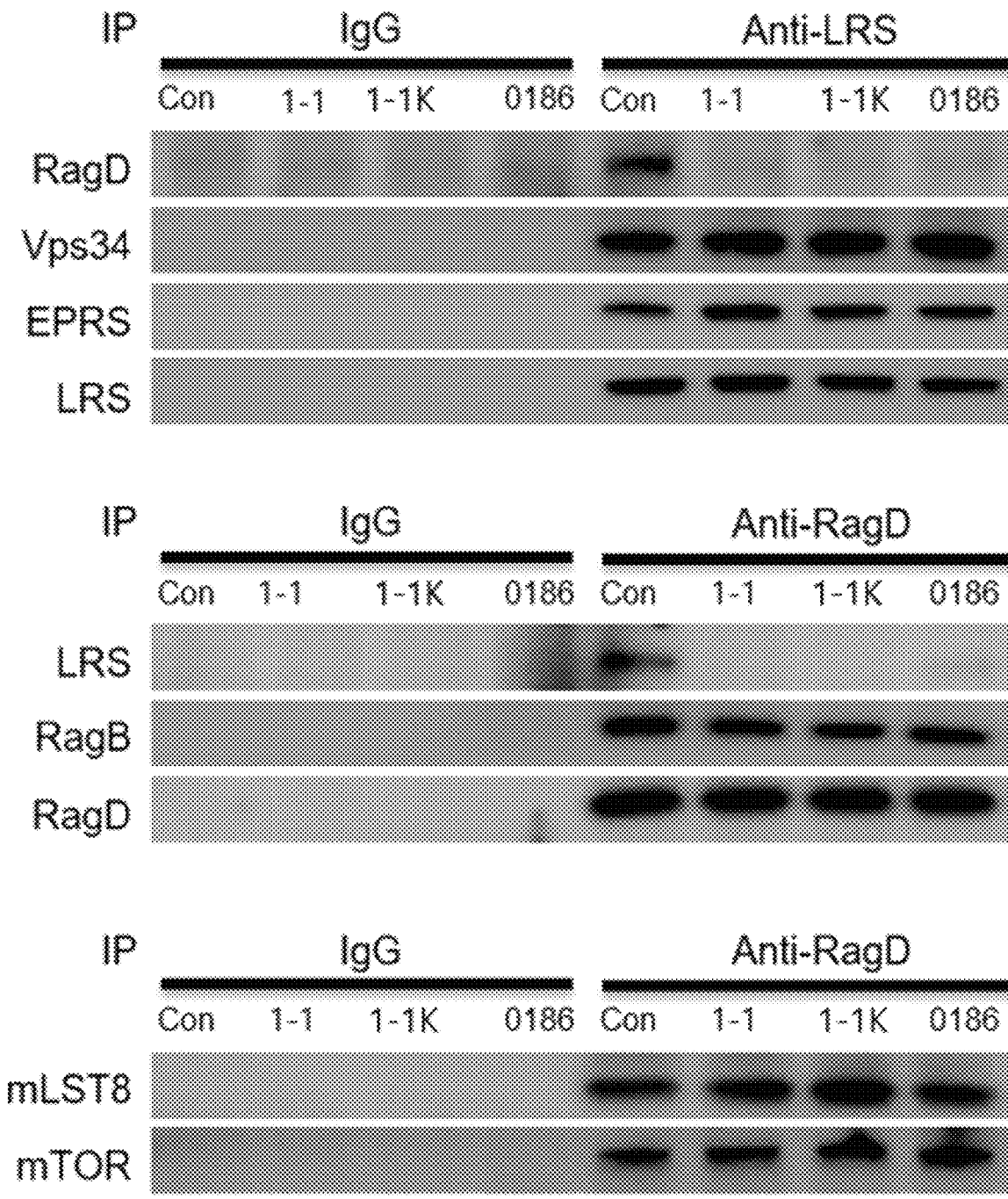
FIG. 3 is an immunoprecipitation result of the inhibition of interaction between LRS and RagD after treatment with the compound of Example 1-1 or a salt thereof on SW620 cells.

The results are shown in FIG. 3.

As shown in FIG. 3, in the control (Con) cells not treated with the compound, both RagD and LRS were detected, it was confirmed that RagD and LRS directly interact. In contrast, in the cells treated with the compound of Example 1-1 or a salt thereof according to the present invention, RagD was hardly detected in the precipitate using the anti-LRS antibody, and in the precipitate using the anti-RagD antibody, almost no LRS was detected, so that their interaction was directly inhibited by the compound of Example 1-1 or a salt thereof.

Example 4: Blood-Brain Barrier (BBB) Permeability Evaluation

After confirming that the compounds of Chemical Formula 1 in the Example 2 exhibit very excellent mTOR inhibitory activity, it was attempted to confirm whether the above compounds could be developed as therapeutic drugs for mTOR pathway-related brain diseases and exhibit high permeability to blood-brain barrier.

4-1. Analysis of in Silico Physicochemical Properties of Compounds

Before evaluating the blood-brain barrier (BBB) permeability of the compounds according to the present invention, the lipophilicity of each compound was predicted using an in silico method. Since one of the most important factors in determining the BBB permeability of a small molecule compound is lipophilicity, evaluating the lipophilicity of each compound before proceeding with the experimental evaluation can be an index that can predict the degree of BBB permeation in advance. To this end, logP, which is a parameter measuring lipophilicity, and molecular polar surface area (PSA) were predicted using the Discovery Studio 2018 program (Dassault Systèmes BIOVIA, Discovery Studio Modeling Environment, Release 2017, San Diego: Dassault Systèmes, 2016)

The LogP value is an index to indicate the fat solubility of a compound, and is a partition coefficient that indicates the ratio of the concentration of the compound dissolved in the water and octanol layer when the compound is dissolved in two unmixed solvents, water and octanol. For example, if the logP value of a particular compound is 3, this means that it has a lipophilicity of about 1000 times better soluble in octanol than water. In order for a specific compound to pass through the blood-brain barrier, the fat-soluble property must be high, but if the fat-soluble property is too high, the blood-brain barrier permeability may be lowered because the compound nonspecifically binds to a substance such as albumin, a plasma protein. It has been reported that the appropriate logP value for penetrating the blood-brain barrier ranges from 1 to 4.

On the other hand, in addition to lipophilicity, the polar surface region (PSA) of the molecule can act as an important factor in determining the blood-brain barrier permeability of the compound (J. Am. Soc. Exp. Neurother. (2005) Vol. 2, 541). PSA is a parameter predicted through 2D approximation of the degree of polar surface of a small molecule compound, and is defined as the surface area occupied by nitrogen and oxygen atoms and polar hydrogens attached to them. This is a number that strongly reflects the hydrogen bonding ability and polarity. In general, the polar surface region is used as a parameter for viewing the tendency of the drug to permeate into the cell, and when it exceeds 140 Å, it tends to not penetrate the cell membrane well.

The logP and PSA values of the compounds of Examples 1-1 to 1-61 of the present invention are shown in Table 4 below.

TABLE 4

Physicochemical properties of compounds in silico analysis

| Example | LogP | PSA |
| --- | --- | --- |
| 1-1 | 3.067 | 104.31 |
| 1-2 | 2.462 | 108.66 |
| 1-3 | 3.273 | 95.52 |
| 1-4 | 3.622 | 95.52 |
| 1-5 | 3.89 | 95.52 |
| 1-6 | 3.273 | 104.31 |
| 1-7 | 3.273 | 104.31 |
| 1-8 | 3.273 | 104.31 |
| 1-9 | 3.732 | 104.31 |
| 1-10 | 3.938 | 95.52 |
| 1-11 | 4.287 | 95.52 |
| 1-12 | 4.555 | 95.52 |
| 1-13 | 3.732 | 104.31 |
| 1-14 | 3.938 | 95.52 |
| 1-15 | 4.287 | 95.52 |
| 1-16 | 4.555 | 95.52 |
| 1-17 | 3.732 | 104.31 |
| 1-18 | 3.938 | 95.52 |
| 1-19 | 4.287 | 95.52 |
| 1-20 | 3.554 | 104.31 |
| 1-21 | 3.76 | 95.52 |

TABLE 4-continued

Physicochemical properties of compounds in silico analysis

| Example | LogP | PSA |
|---|---|---|
| 1-22 | 4.108 | 95.52 |
| 1-23 | 4.376 | 95.52 |
| 1-24 | 4.262 | 104.31 |
| 1-25 | 4.816 | 95.52 |
| 1-26 | 4.922 | 104.31 |
| 1-27 | 5.477 | 95.52 |
| 1-28 | 4.04 | 104.31 |
| 1-29 | 4.595 | 95.52 |
| 1-30 | 3.051 | 113.54 |
| 1-31 | 3.976 | 104.31 |
| 1-32 | 4.531 | 95.52 |
| 1-33 | 2.456 | 117.2 |
| 1-34 | 2.122 | 128.63 |
| 1-35 | 1.917 | 117.2 |
| 1-36 | 1.583 | 128.63 |
| 1-37 | 3.213 | 104.31 |
| 1-38 | 3.496 | 104.31 |
| 1-39 | 2.168 | 89.29 |
| 1-40 | 2.374 | 89.29 |
| 1-41 | 2.374 | 89.29 |
| 1-42 | 2.374 | 89.29 |
| 1-43 | 2.833 | 89.29 |
| 1-44 | 2.833 | 89.29 |
| 1-45 | 2.833 | 89.29 |
| 1-46 | 2.655 | 89.29 |
| 1-47 | 3.362 | 89.29 |
| 1-48 | 4.023 | 89.29 |
| 1-49 | 3.141 | 89.29 |
| 1-50 | 2.152 | 98.52 |
| 1-51 | 3.077 | 89.29 |
| 1-52 | 1.018 | 102.18 |
| 1-53 | 2.451 | 89.29 |
| 1-54 | 2.596 | 89.29 |
| 1-55 | 4.16 | 104.31 |
| 1-56 | 2.884 | 117.2 |
| 1-57 | 2.345 | 117.2 |
| 1-58 | 2.597 | 89.29 |
| 1-59 | 1.985 | 102.18 |
| 1-60 | 1.446 | 102.18 |
| 1-61 | 1.446 | 102.18 |

4-2. In vitro blood-brain barrier (BBB) permeability evaluation

Specifically, the Pion BBB-PAMPA assay kit was used as an in vitro model of passive and intercellular permeability. An artificial membrane immobilized on the filter was placed between the donor and acceptor compartments. Each of the selected compounds was introduced into the donor compartment, and then the drug concentration in the donor and receptor compartments was measured to evaluate the BBB permeability of the compound of Chemical Formula 1 and the positive control group.

Figure 4:
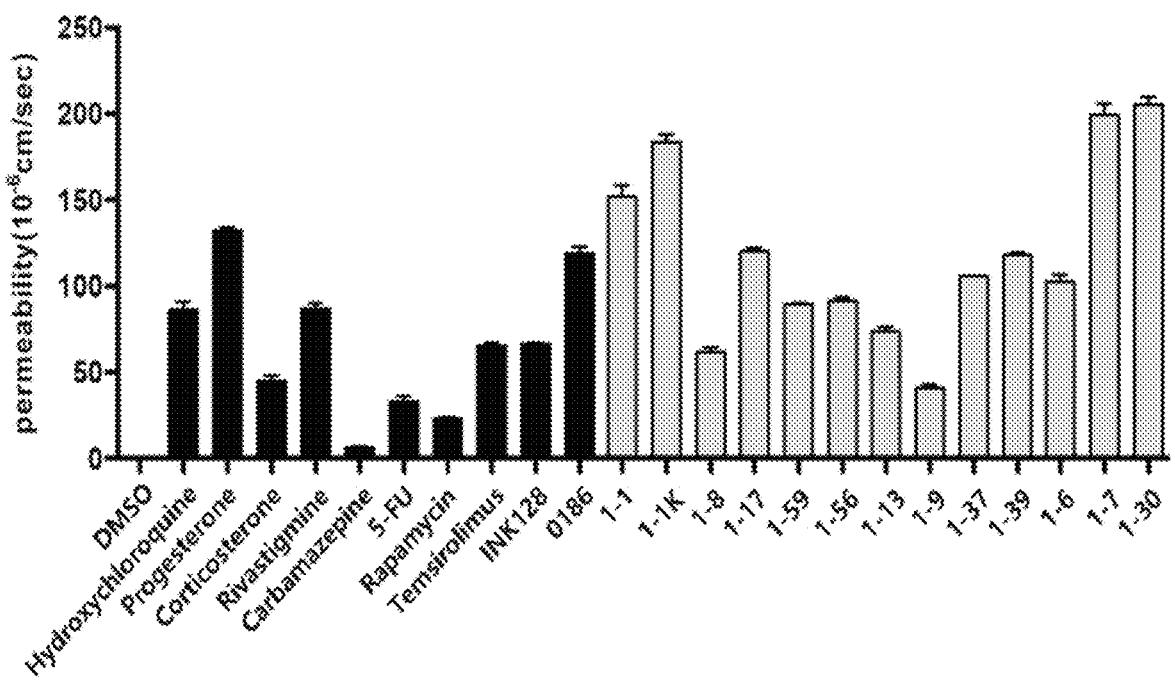
FIG. 4 is a result of analyzing the blood-brain barrier (BBB) permeability of compounds according to the present invention using an in vitro Pion BBB-PAMPA assay kit.

The results are shown in FIG. 4.

As shown in FIG. 4, the compounds according to the present invention show excellent artificial membrane permeability results even compared to hydroxychloroquine, progesterone, corticosterone, rivastigmine, carbamazepine and 5-FU, which are used as treatments for brain diseases, and it was also confirmed that it showed the best permeability in comparison with mTOR inhibitors (rapamycin, temsirolimus, INK128). In addition, it was confirmed that it exhibited a permeability equal to or higher than that of the compound of Example 1-214 described in Korean Patent Laid-Open Patent No. 10-2017-0107404, which is known to exhibit mTOR activity inhibitory effect (indicated as "0186" in the Figures).

Example 5: In Vivo mTOR Inhibitory Activity and BBB Permeability Evaluation

After 7-week-old C57BL/6 male mice were intraperitoneally administered the salt (1-1K) of the compound of the Example 1-1 or rapamycin as a positive control every 7 days, the effect of the compound on the activation of mTOR was evaluated by analyzing the degree of phosphorylation of S6K in the brain's neocortex and hippocampus.

The salt of the compound of the Example 1-1 was administered at a dose of 100 mg/kg (in 10% DMAC, 15% Tween 80, 75% 0.1M Na2HPO4, pH9.4), and rapamycin at a dose of 2 mg/kg (in 10% DMAC, 15% Tween 80, 75% saline).

Figure 5:
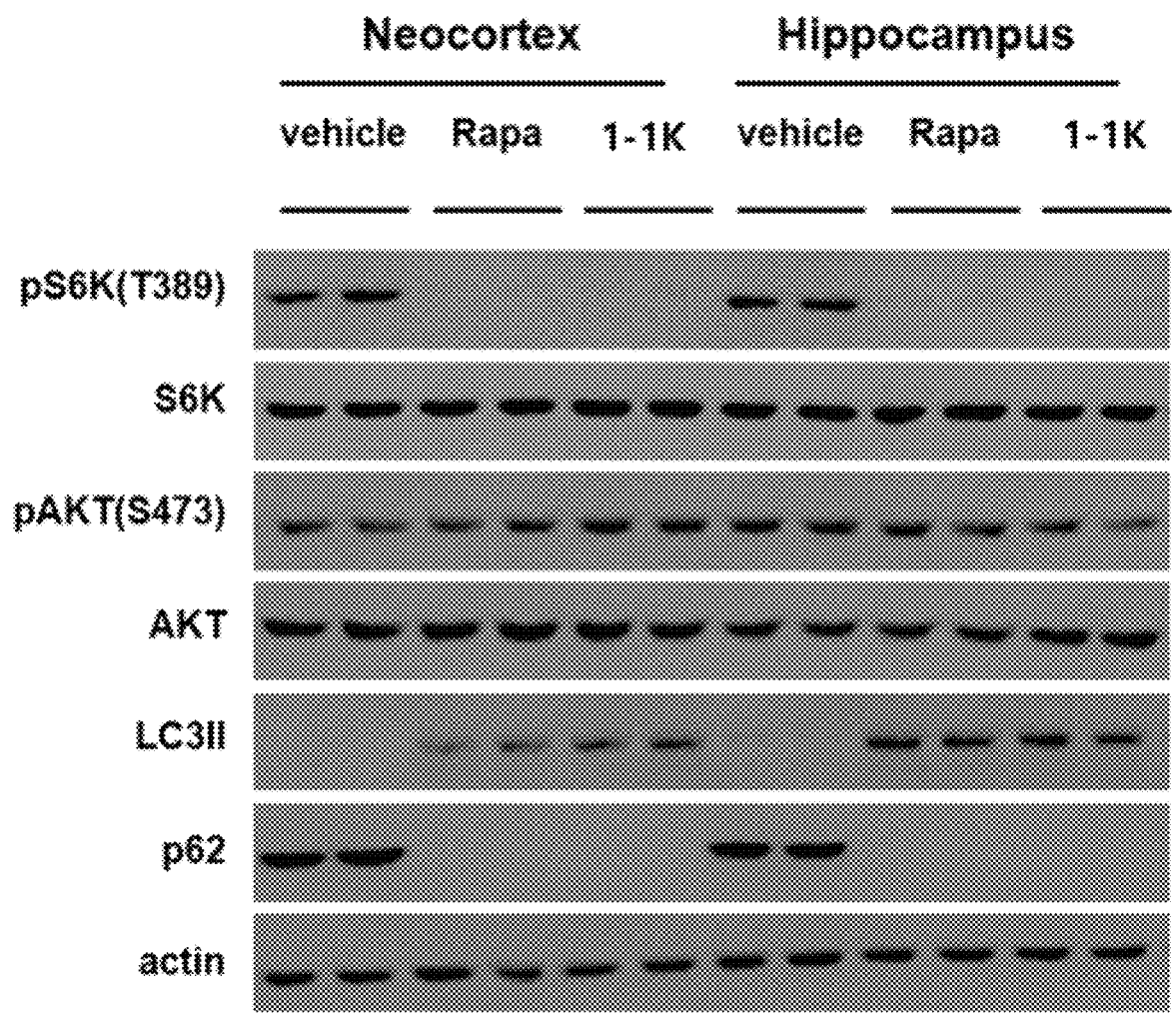
FIG. 5 is an immunoblot result of the phosphorylation and expression of S6K in brain neocortex and hippocampus of a 7-week-old C57BL/6 male mouse with intraperitoneal administration of a salt (100 mg/kg) of the compound of Example 1 or rapamycin (Rapa, 2 mg/kg).

The results are shown in FIG. 5.

As shown in FIG. 5, it was confirmed that phosphorylated S6K was not detected in the animals to which the salt of the compound of Example 1-1 was administered, so that the activity of mTORC1 was inhibited by treatment with the compound.

On the other hand, it was found that the phosphorylation degree of AKT was not changed by the salt treatment of the compound of Example 1-1, so that the activity of mTORC2 was not inhibited, it was found that the autophagy action, which can be confirmed from the degradation of LC3 II or p62, was increased by treatment with the compound.

On the other hand, the present inventor attempted to evaluate the mTOR. inhibitory activity by salt concentration of the compound of Example 1-1 based on the above results. That is, after administering salts 0, 1, 2.5, 5, 10, 20, and 50 mg/kg of the compound of Example 1-1 to the animal in the same manner as the above experimental method, the degree of phosphorylation of S6K and protein expression in the renal cortex and hippocampus of the brain were analyzed.

Figure 6:
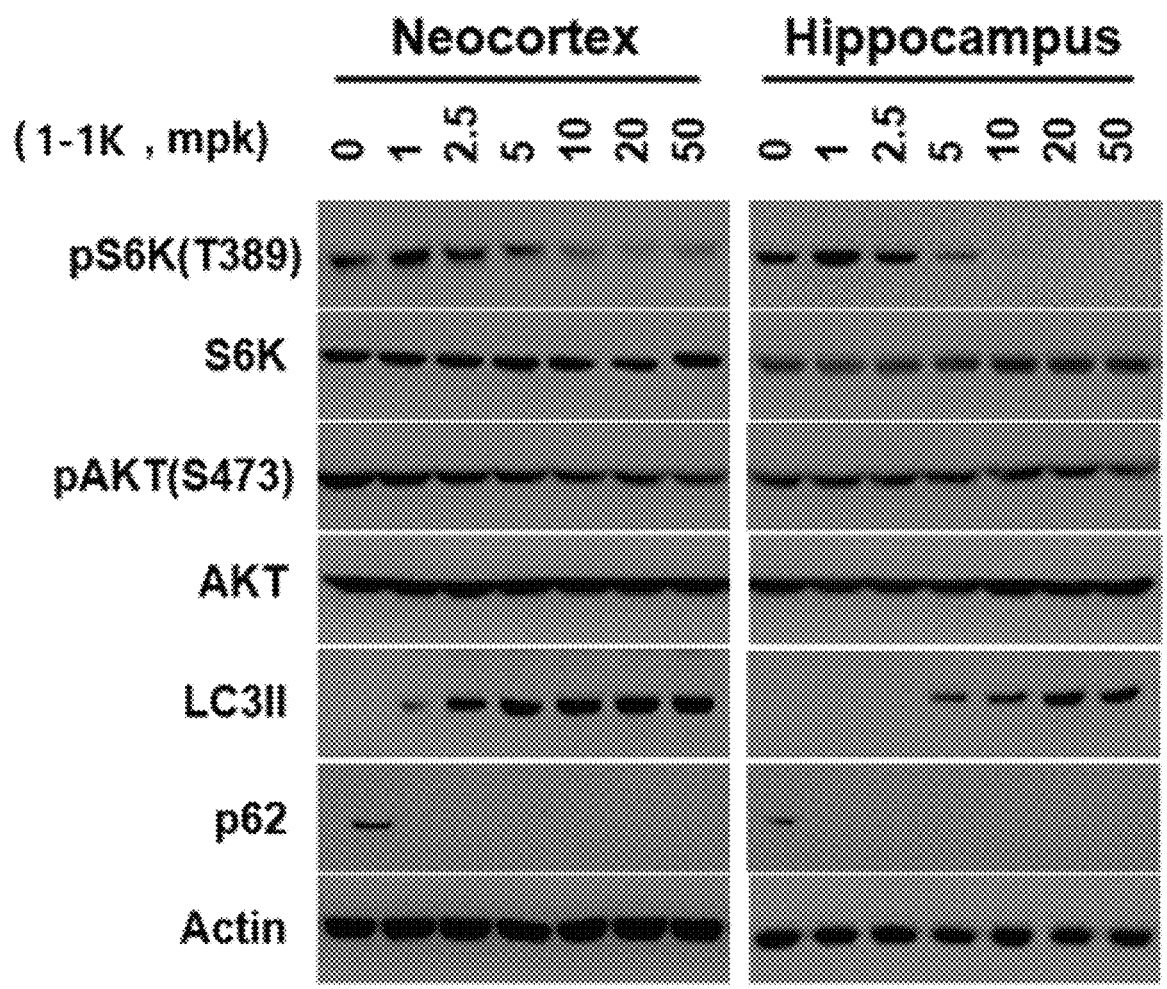
FIG. 6 is an immunoblot result of the phosphorylation and expression of S6K in brain neocortex and hippocampus of a 7-week-old C57BL/6 male mouse with intraperitoneal administration of a salt of the compound of Example 1-1 at various concentrations.

The results are shown in FIG. 6.

As shown in FIG. 6, it was confirmed that the salt of the compound of Example 1-1 inhibited the phosphorylation of S6K in the brain of the animal in a concentration-dependent manner, which means that it could be determined that the salt of the compound of Example 1-1 penetrated the blood-brain barrier of the animal in a concentration-dependent manner, thereby exhibiting mTOR inhibitory activity.

As described above, it was found that the compound of the Chemical Formula 1 according to the present invention exhibits excellent mTOR inhibitory activity and blood-brain barrier permeability, so that it may be very useful as a therapeutic agent for brain diseases related to the mTOR pathway.

Example 6: Evaluation of Amyloid Plaque Removal Ability in Alzheimer's Animal Model In the experiment, 7 months old male B6C3H/APP/PS1 mice were purchased from Jackson Lab (Bar Harbor, Me., USA) and used. These mouse are all dual transgenic mice expressing chimeric mouse/human amyloid precursor protein and mutant human presenilin 1, both of these are about CNS neurons. Both mutations are associated with early onset Alzheimer's.

The prepared salt (1-4K) of the compound of Example 1-1 was intraperitoneally administered at 0, 5, 10 or 20 mpk (mg/kg) per mouse, once daily for 7 days. As the solvent, 10% DMAC, 15% Tween 80, and 75% 0.1M Na2HPO4 buffer were used.

For immunohistochemical analysis, mice were anesthetized with 2% Avertin (20 μg $g^{-1}$, intraperitoneally), perfused with 0.9% saline, and perfused with ice-cold 4% paraformaldehyde. Excised brains of B6C3H/APP/PS1 mice were fixed in 4% paraformaldehyde (pH 7.4) for 16 hours. The fixed brain samples were immersed in 30% sucrose for cryoprotection and sliced to a thickness of 35 μm using a Cryostat (Microm HM 525, Thermo Scientific, Waltham, Mass., USA). To visualize Aβ plaques, sliced brain sections were stained with thioflavin S (ThS) for 7 minutes. Thioflavin S was purchased from Sigma-Aldrich (catalog number T-1892). 500 μM of Thioflavin S (ThS) was dissolved in 50% ethanol. After successive washing with 100%, 95% and 70% ethanol, the sections were transferred to PBS.

For immunofluorescence, relatively thick free floating brain sections were incubated with goat anti-GFAP antibody for 7 days at 4° C. The sections were then incubated overnight at 4° C. with Alexa Fluor 594-conjugated donkey anti-goat IgG (1:200, Abcam, ab150132). Nuclear control staining was performed using 4'6'-diamino-2-phenylindole dihydrochloride hydrate (DAPI, 1 mg/mL, 1:2000, Sigma).

Images were taken with a Leica DM2500 fluorescence microscope. Plaque numbers were calculated from a single brain image of each mouse using the ImageJ software program.

Figure 7:
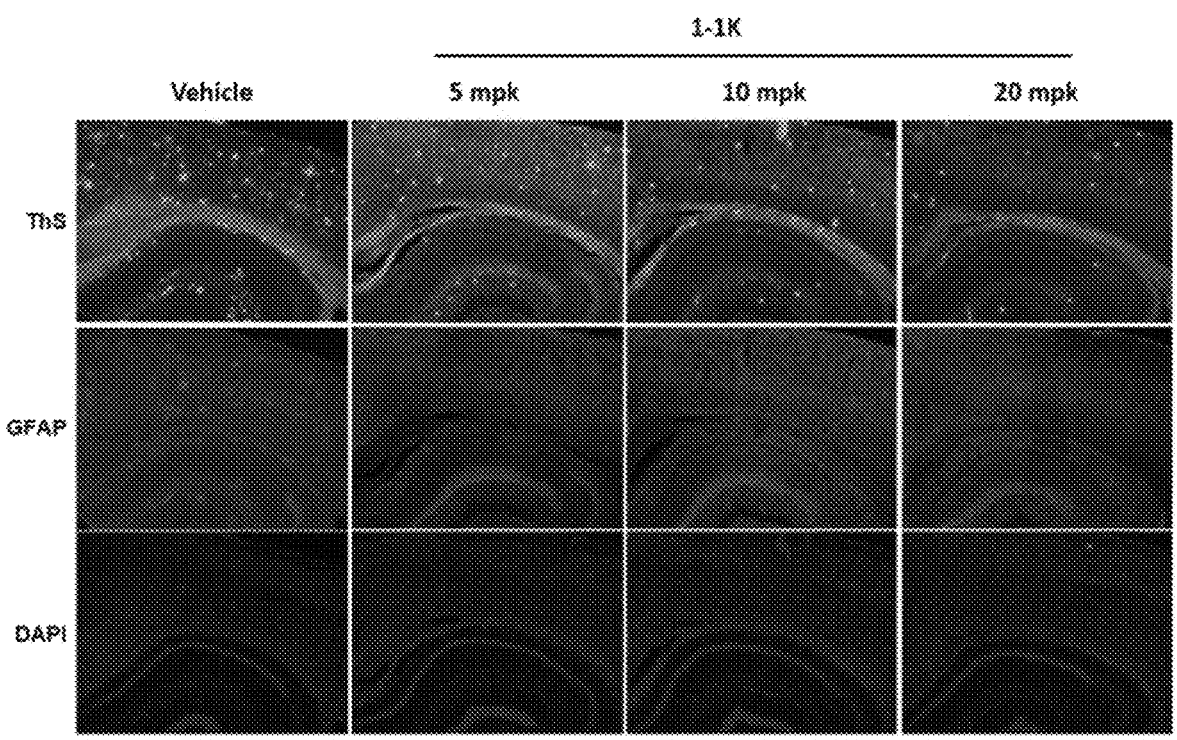
FIG. 7 is a ThS-staining result of amyloid β plaques in the hippocampus of an Alzheimer's animal model mouse intraperitoneally administered for 7 days with a salt of the compound of Example 1-1 (0, 5, 10 or 20 mg/kg).
Figure 8:
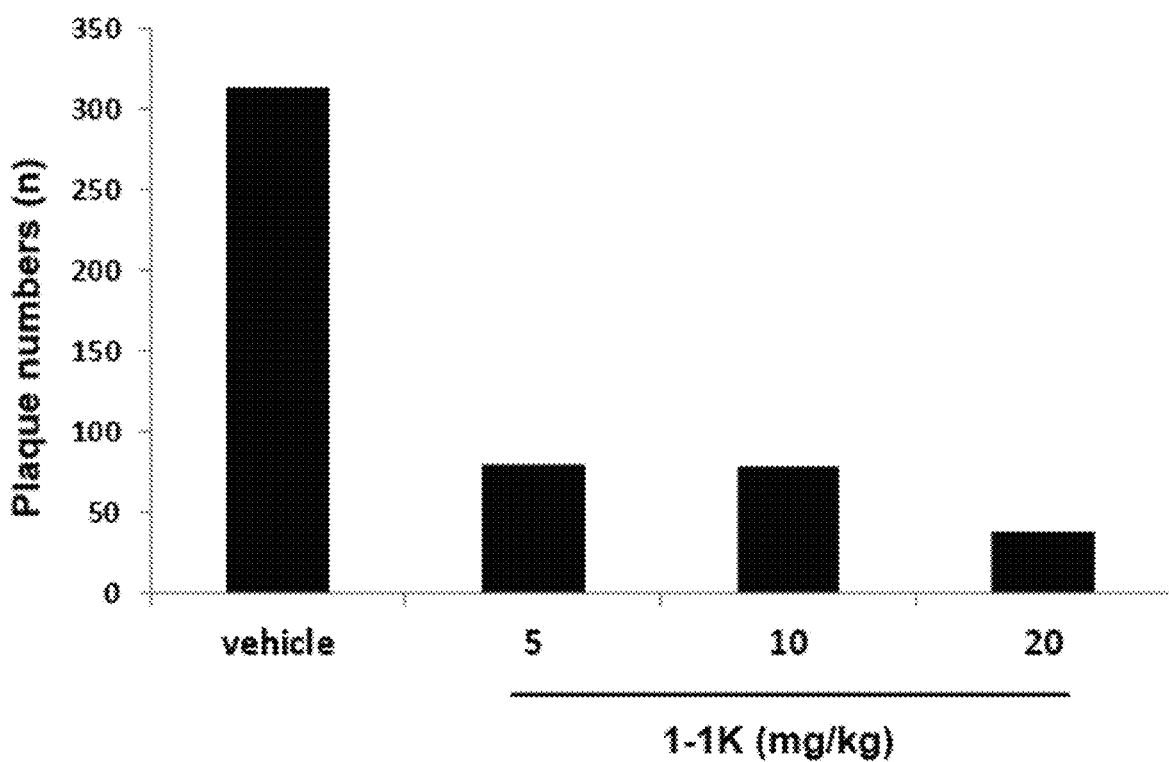
FIG. 8 is a result of quantifying ThS-positive amyloid plaques in the whole brain of Alzheimer's animal model mice intraperitoneally administered with a salt of the compound of Example 1-1 (0, 5, 10 or 20 mg/kg) for 7 days.

The results are shown in FIGS. 7 and 8.

Aβ deposition in the brain of APP/PS1 mice can be detected at 6 months of age. To investigate the effect of Examples 1-1K on Aβ deposits, ThS staining for amyloid plaques in fixed brain tissue was performed.

As can be seen in FIGS. 7 and 8, amyloid plaque deposits were significantly reduced in the brains of Example 1-1K-treated APP/PS1 mice than in the brains of solvent-administration control(vehicle) APP/PS1 mice. Through this, it was confirmed that the compound treatment of the present invention alleviates the deposition of amyloid plaques.

Example 7: Evaluation of Inhibitory Activity of mTORC1 in TSC CKO Epilepsy Animal Model Animal care was performed according to an animal protocol approved by the Animal Experiment Committee of Seoul National University. TSC2$^{GFAP1}$ CKO mice were generated as follows. TSC2$^{flox/flox}$ mice were first crossed with the same GFAP-Cre mouse line. The resulting TSC2$^{flox/+}$; TSC2$^{flox/flox}$ by crossing GFAP-Cre mice with other TSC2$^{flox/flox}$ mice; GFAP-Cre mice were generated. Rapamycin (3 mg/kg) and the compound of Example 1-1K (10 mg/kg) were injected intraperitoneally (I.P.) 4 times daily. Rapamycin and the compound of Example 1-1K were dissolved in injection buffer (10% DMAC, 15% TWEEN80, 75% 0.1M Na2HPO4 buffer).

For western blot analysis, mouse cerebral neocortex and hippocampus were dissected and sonicated in cell lysis buffer (Cell Signaling, Beverly, Mass., USA). After centrifugation at 15,000 rpm at 4° C. for 1 hour. a supernatant was obtained and the protein concentration was measured by the Bradford method (Pierce, Rockford, Ill., USA). An equal amount of total protein extract was separated by SDS-PAGE and transferred to a nitrocellulose membrane. After incubation with anti-p-S6K (T389) (Cell Signaling, #9205), anti-S6K (Cell Signaling, #9202), anti-Actin (Santa Cruz Biotechnology, #sc-1616), anti-p-AKT (S473) (Cell signaling, #4060), anti-AKT (Cell signaling, #2920) anti-p62/SQSTM1 (Cell signaling, #39749) and anti-LC3A (Cell signaling, #4108) antibodies in 1% TTBBS buffer (10 mM Tris, 10% Tris (Tris-HCl, pH 7.5, 150 mM NaCl, 0.05% Tween 20), the membrane was reacted with a peroxidase-conjugated secondary antibody. Signals were detected using an improved chemiluminescent reagent (Pierce, Rockford, Ill., USA).

Figure 9:
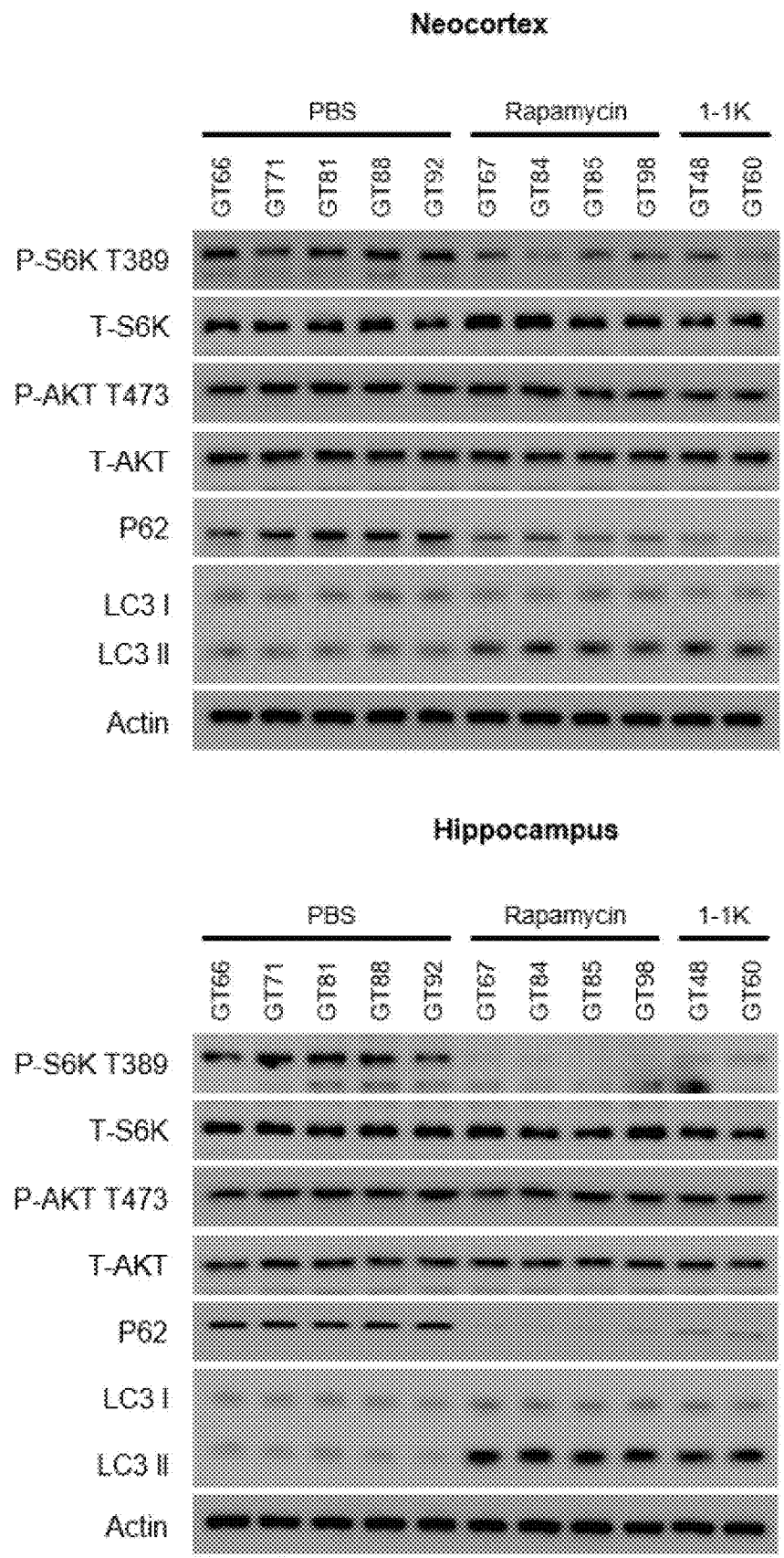
FIG. 9 is western blot of showing alteration of mTORC1 activation (p-S6K (T389)) expression), mTORC2 activation (p-AKT (S473) expression) and autophagy markers (LC3 II increment or p62 cleavage) after rapamycin (3 mg/kg) or a salt of the compound of Example 1-1 (10 mg/kg) was administrated intraperitoneally to a TSC2 CKO epilepsy animal model mouse for 4 weeks.

The results are shown in FIG. 9.

FIG. 9 shows phospho-S6K (T389) levels in the cerebral cortex and hippocampus of TSC2 CKO mice administered with each test substance for 4 weeks. As reflected in the expression of p-S6K (T389), mTORC1 activation was confirmed to be reduced in mice administered rapamycin or Example 1-1K compared to the control group. mTORC2 activation was not affected by rapamycin or Examples 1-1K as reflected by p-AKT (S473). Consistent with mTORC1 inhibition, autophagy (LC3 II increase or p62 cleavage) was found to be induced by rapamycin or Examples 1-1K.

INDUSTRIAL APPLICABILITY

The compound represented by the Chemical Formula 1 according to the present invention has a very excellent effect of inhibiting mTORC1 and blood-brain barrier permeability, and it has excellent industrial applicability as it can be used very usefully in the development of prevention or treatments of brain diseases related to the mTOR pathway.

What is claimed is:
1. A compound defined by Chemical Formula 1 or pharmaceutically acceptable salt thereof:

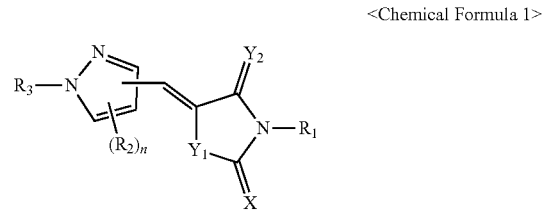

<Chemical Formula 1> wherein R1 is hydrogen; substituted or unsubstituted C1-C5 straight or branched alkyl; C2-C5 alkenyl; C3-C10 heteroarylalkyl; or C1-C5 hydroxyalkyl;
R2 is hydrogen; C1-C5 straight or branched alkyl;
R3 is hydrogen; substituted or unsubstituted C1-C5 straight or branched alkyl;
C6-C15 aryl; or C3-C15 heteroaryl;
X is oxygen, sulfur, or nitrogen;
Y1 and Y2 are each independently oxygen or sulfur; and
n is 0, 1, or 2; and
wherein the compound defined by Chemical Formula 1 or pharmaceutically acceptable salt thereof is selected from the group consisting of (5Z)-5-[(1-phenylpyrazol-4-yl)methylene]-2-thioxo-thiazolidin-4-one, (5Z)-3-(2-furylmethyl)-5-[(1-methylpyrazol-4-yl)methylene]-2-thioxo-thiazolidin-4-one, (5Z)-3-methyl-5-[(1-phenylpyrazol-4-yl)methylene]-2-thioxo-thiazolidin-4-one, (5Z)-3-allyl-5-[(1-phenylpyrazol-4-yl)methylene]-2-thioxo-thiazolidin-4-one, (5Z)-5-[[1-(2-fluorophenyl)pyrazol-4-yl]methylene]-2-thioxo-thiazolidin-4-one, (5Z)-5-[[1-(3-fluorophenyl)pyrazol-4-yl]methylene]-2-thioxo-thiazolidin-4-one, (5Z)-5-[[1-(4-fluorophenyl)pyrazol-4-yl]methylene]-2-thioxo-thiazolidin-4-one, (5Z)-5-[[1-(2-chlorophenyl)pyrazol-4-yl]methylene]-2-thioxo-thiazolidin-4-one, (5Z)-5-[[1-(2-chlorophenyl)pyrazol-4-yl]methylene]-3-methyl-2-thioxo-thiazolidin-4-one, (5Z)-5-[[1-(2-chlorophenyl)pyrazol-4-yl]methylene]-3-ethyl-2-thioxo-thiazolidin-4-one, (5Z)-3-allyl-5-[[1-(2- chlorophenyl)pyrazol-4-yl]methylene]-2-thioxo-thiazolidin-4-one, (5Z)-5-[[1-(3-chlorophenyl)pyrazol-4-yl]methylene]-2-thioxo-thiazolidin-4-one, (5Z)-5-[[1-(3-chlorophenyl)pyrazol-4-yl]methylene]-3-methyl-2-thioxo-thiazolidin-4-one, (5Z)-5-[[1-(3-chlorophenyl) pyrazol-4-yl]methylene]-3-ethyl-2-thioxo-thiazolidin-4-one, (5Z)-3-allyl-5-[[1-(3-chlorophenyl)pyrazol-4-yl]methylene]-2-thioxo-thiazolidin-4-one, (5Z)-5-[[1-(4-chlorophenyl)pyrazol-4-yl]methylene]-2-thioxo-thiazolidin-4-one, (5Z)-5-[[1-(4-chlorophenyl)pyrazol-4-yl]methylene]-3-methyl-2-thioxo-thiazolidin-4-one, (5Z)-5-[[1-(4-chlorophenyl)pyrazol-4-yl]methylene]-3-ethyl-2-thioxo-thiazolidin-4-one, (5Z)-5-[[1-(p-tolyl)pyrazol-4-yl]methylene]-2-thioxo-thiazolidin-4-one, (5Z)-3-methyl-5-[[1-(p-tolyl)pyrazol-4-yl]methylene]-2-thioxo-thiazolidin-4-one, (5Z)-3-ethyl-5-[[1-(p-tolyl)pyrazol-4-yl]methylene]-2-thioxo-thiazolidin-4-one, (5Z)-3-allyl-5-[[1-(p-tolyl)pyrazol-4-yl]methylene]-2-thioxo-thiazolidin-4-one, (5Z)-5-[[1-(4-isopropylphenyl)pyrazol-4-yl]methylene]-2-thioxo-thiazolidin-4-one, (5Z)-3-ethyl-5-[[1-(4-isopropylphenyl)pyrazol-4-yl]methylene]-2-thioxo-thiazolidin-4-one, (5Z)-5-[[1-(4-butylphenyl)pyrazol-4-yl]methylene]-2-thioxo-thiazolidin-4-one, (5Z)-5-[[1-(4-butylphenyl)pyrazol-4-yl]methylene]-3-ethyl-2-thioxo-thiazolidin-4-one, (5Z)-5-[[1-(3,4-dimethylphenyl)pyrazol-4-yl]methylene]-2-thioxo-thiazolidin-4-one, (5Z)-5-[[1-(3,4-dimethylphenyl)pyrazol-4-yl]methylene]-3-ethyl-2-thioxo-thiazolidin-4-one, (5Z)-5-[[1-(2-methoxyphenyl)pyrazol-4-yl]methylene]-2-thioxo-thiazolidin-4-one, (5Z)-5-[[1-(2-naphthyl)pyrazol-4-yl]methylene]-2-thioxo-thiazolidin-4-one, (5Z)-3-ethyl-5-[[1-(2-naphthyl)pyrazol-4-yl]methylene]-2-thioxo-thiazolidin-4-one, (5Z)-5-[[1-(2-pyridyl)pyrazol-4-yl]methylene]-2-thioxo-thiazolidin-4-one, (5Z)-3-(2-hydroxyethyl)-5-[[1-(2-pyridyl)pyrazol-4-yl]methylene]-2-thioxo-thiazolidin-4-one, (5Z)-5-[[1-(3-pyridyl)pyrazol-4-yl]methylene]-2-thioxo-thiazolidin-4-one, (5Z)-3-(2-hydroxyethyl)-5-[[1-(3-pyridyl)pyrazol-4-yl]methylene]-2-thioxo-thiazolidin-4-one, (5Z)-5-[(5-methyl-1-phenyl-pyrazol-4-yl)methylene]-2-thioxo-thiazolidin-4-one, (5Z)-5-[(3,5-dimethyl-1-phenyl-pyrazol-4-yl)methylene]-2-thioxo-thiazolidin-4-one, (5Z)-5-[(1-phenylpyrazol-4-yl)methylene]thiazolidine-2,4-dione, (5Z)-5-[[1-(2-fluorophenyl)pyrazol-4-yl]methylene]thiazolidine-2,4-dione, (5Z)-5-[[1-(3-fluorophenyl)pyrazol-4-yl]methylene]thiazolidine-2,4-dione, (5Z)-5-[[1-(4-fluorophenyl)pyrazol-4-yl]methylene]thiazolidine-2,4-dione (5Z)-5-[[1-(2-chlorophenyl)pyrazol-4-yl]methylene]thiazolidine-2,4-dione, (5Z)-5-[[1-(3-chlorophenyl)pyrazol-4-yl]methylene]thiazolidine-2,4-dione, (5Z)-5-[[1-(4-chlorophenyl)pyrazol-4-yl]methylene]thiazolidine-2,4-dione, (5Z)-5-[[1-(p-tolyl)pyrazol-4-yl]methylene]thiazolidine-2,4-dione, (5Z)-5-[[1-(4-isopropylphenyl)pyrazol-4-yl]methylene]thiazolidine-2,4-dione, (5Z)-5-[[1-(4-butylphenyl)pyrazol-4-yl]methylene]thiazolidine-2,4-dione, (5Z)-5-[[1-(3,4-dimethylphenyl)pyrazol-4-yl]methylene]thiazolidine-2,4-dione, (5Z)-5-[[1-(2-methoxyphenyl)pyrazol-4-yl]methylene]thiazolidine-2,4-dione, (5Z)-5-[[1-(2-naphthyl)pyrazol-4-yl]methylene]thiazolidine-2,4-dione, (5Z)-5-[[1-(3-pyridyl)pyrazol-4-yl]methylene]thiazolidine-2,4-dione, (5Z)-5-[(3-methyl-1-phenyl-pyrazol-4-yl)methylene]thiazolidine-2,4-dione, (5Z)-5-[(3,5-dimethyl-1-phenyl-pyrazol-4-yl)methylene]thiazolidine-2,4-dione, (5Z)-5-[[1-(4-chlorophenyl)pyrazol-3-yl]methylene]-2-thioxo-thiazolidin-4-one, (5Z)-5-[[1-(2-pyridyl)pyrazol-3-yl]methylene]-2-thioxo-thiazolidin-4-one, (5Z)-5-[[1-(3-pyridyl)pyrazol-3-yl]methylene]-2-thioxo-thiazolidin-4-one, (5Z)-5-[[1-phenylpyrazol-3-yl]methylene]thiazolidine-2,4-dione, (5Z)-5-[[1-(2-pyridyl)pyrazol-3-yl]methylene]thiazolidine-2,4-dione, (5Z)-5-[[1-(3-pyridyl)pyrazol-3-yl]methylene]thiazolidine-2,4-dione, and (5Z)-5-[[1-(4-pyridyl)pyrazol-3-yl]methylene]thiazolidine-2,4-dione.

2. The compound or pharmaceutically acceptable salt thereof of claim 1, wherein the compound is selected from the group consisting of (5Z)-5-[(1-phenylpyrazol-4-yl)methylene]-2-thioxo-thiazolidin-4-one, (5Z)-5-[[1-(2-fluorophenyl)pyrazol-4-yl]methylene]-2-thioxo-thiazolidin-4-one, (5Z)-5-[[1-(3-fluorophenyl)pyrazol-4-yl]methylene]-2-thioxo-thiazolidin-4-one, (5Z)-5-[[1-(4-fluorophenyl)pyrazol-4-yl]methylene]-2-thioxo-thiazolidin-4-one, (5Z)-5-[[1-(2-chlorophenyl)pyrazol-4-yl]methylene]-2-thioxo-thiazolidin-4-one, (5Z)-5-[[1-(3-chlorophenyl)pyrazol-4-yl]methylene]-2-thioxo-thiazolidin-4-one, (5Z)-5-[[1-(4-chlorophenyl)pyrazol-4-yl]methylene]-2-thioxo-thiazolidin-4-one, (5Z)-5-[[1-(4-isopropylphenyl)pyrazol-4-yl]methylene]-2-thioxo-thiazolidin-4-one, (5Z)-5-[[1-(2-methoxyphenyl)pyrazol-4-yl]methylene]-2-thioxo-thiazolidin-4-one, (5Z)-5-[[1-(2-pyridyl)pyrazol-4-yl]methylene]-2-thioxo-thiazolidin-4-one, (5Z)-5-[[1-(3-pyridyl)pyrazol-4-yl]methylene]-2-thioxo-thiazolidin-4-one, (5Z)-5-[(5-methyl-1-phenyl-pyrazol-4-Amethylene]-2-thioxo-thiazolidin-4-one, (5Z)-5-[(1-phenylpyrazol-4-yl)methylene]thiazolidine-2,4-dione, (5Z)-5-[[1-(3-pyridyl)pyrazol-4-yl]methylene]thiazolidine-2,4-dione, (5Z)-5-[[1-(2-pyridyl)pyrazol-3-yl]methylene]-2-thioxo-thiazolidin-4-one, (5Z)-5-[[1-(3-pyridyl)pyrazol-3-yl]methylene]-2-thioxo-thiazolidin-4-one, (5Z)-5-[[1-(2-pyridyl)pyrazol-3-yl]methylene]thiazolidine-2,4-dione, and (5Z)-5-[[1-(4-pyridyl)pyrazol-3-yl]methylene]thiazolidine-2,4-dione.

3. The compound or pharmaceutically acceptable salt thereof of claim 1, wherein the compound is (5Z)-5-[(1-phenylpyrazol-4-yl)methylene]-2-thioxo-thiazolidin-4-one.

4. The compound or pharmaceutically acceptable salt thereof of claim 1, wherein the compound or pharmaceutically acceptable salt thereof is the potassium salt of (5Z)-5-[(1-phenylpyrazol-4-yl)methylene]-2-thioxo-thiazolidin-4-one.

5. A method for preparing the compound of claim 1 or pharmaceutically acceptable salt thereof using Reaction Scheme 1:

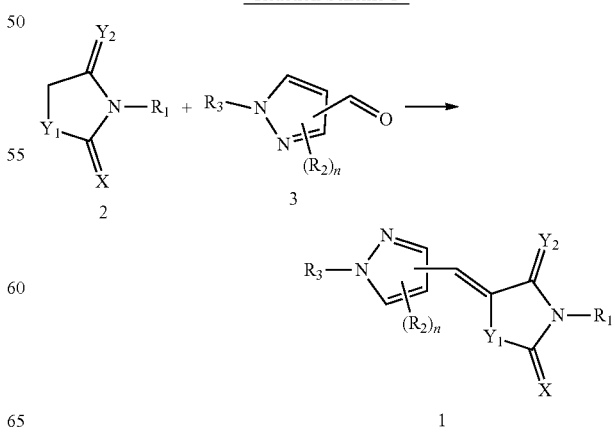

wherein $R_1$, $R_2$, $R_3$, X, $Y_1$, $Y_2$ and n are described in claim 1.

6. A pharmaceutical composition comprising the compound of claim 1 or pharmaceutically acceptable salt thereof as an active ingredient and a pharmaceutically acceptable carrier.

7. A method for treating a brain disease associated with mTOR (mechanistic target of rapamycin) pathway in a subject in need thereof, the method comprising administering an effective amount of a composition comprising the compound of claim 1 or pharmaceutically acceptable salt thereof as an active ingredient to the subject in need thereof.

8. The method of claim 7, wherein the brain disease associated with mTOR pathway is selected from the group consisting of epilepsy, Alzheimer's disease, Huntington's disease, depression, Parkinson's disease, Tuberous sclerosis, Autism spectrum disorder, Cowden syndrome, Bannayan-Riley-Ruvacalba syndrome, Lhermitte-Duclos disease, Neurofibromatosis, Neurofibromatosis Type 1, Autism, Non-syndromic autism, and Schizophrenia.

* * * * *